US012663982B2

(12) United States Patent
Fields et al.

(10) Patent No.: US 12,663,982 B2
(45) Date of Patent: Jun. 23, 2026

(54) AUTONOMOUS VEHICLE ACCIDENT AND EMERGENCY RESPONSE

(71) Applicant: State Farm Mutual Automobile Insurance Company, Bloomington, IL (US)

(72) Inventors: Brian Mark Fields, Normal, IL (US); Chien Che Huang, Normal, IL (US); Mohamed A. Wazeer, Normal, IL (US); Shawn C. Bennett, Le Roy, IL (US); Steven C. Cielocha, Bloomington, IL (US); Ronny S. Bryant, Bloomington, IL (US); Stephen Kohaus, Bloomington, IL (US); Terry Quakenbush, Normal, IL (US); Richard A. Novak, Bloomington, IL (US); Craig M. Main, Hagerstown, MD (US); Weixin Wu, Aurora, IL (US); Torri Wollenschlager, Bloomington, IL (US); Carol Marie Csanda, Normal, IL (US); Stacey Gorsuch, Bloomington, IL (US); Todd Binion, Bloomington, IL (US); Aaron Scott Chan, Lisle, IL (US)

(73) Assignee: State Farm Mutual Automobile Insurance Company, Bloomington, IL (US)

( * ) Notice: Subject to any disclaimer, the term of this patent is extended or adjusted under 35 U.S.C. 154(b) by 0 days.

(21) Appl. No.: 18/765,905

(22) Filed: Jul. 8, 2024

(65) Prior Publication Data

US 2024/0362013 A1      Oct. 31, 2024

Related U.S. Application Data

(63) Continuation of application No. 18/134,365, filed on Apr. 13, 2023, now Pat. No. 12,032,945, which is a (Continued)

(51) Int. Cl.
| | | |
|---|---|---|
| *G06F 8/65* | (2018.01) | |
| *A61B 5/00* | (2006.01) | |

(Continued)

(52) U.S. Cl.
CPC ............ *G06F 8/65* (2013.01); *A61B 5/02028* (2013.01); *A61B 5/4064* (2013.01);
(Continued)

(58) Field of Classification Search
CPC ..... G06F 8/65; A61B 5/02028; A61B 5/4064; A61B 5/4094; A61B 5/6893;
(Continued)

(56) References Cited

U.S. PATENT DOCUMENTS

| | | |
|---|---|---|
| 7,103,460 B1 | 9/2006 | Breed |
| 8,665,118 B1 | 3/2014 | Woodard et al. |

(Continued)

FOREIGN PATENT DOCUMENTS

| | | |
|---|---|---|
| EP | 3239686 A1 | 11/2017 |
| EP | 3578433 A1 | 4/2019 |

(Continued)

OTHER PUBLICATIONS

Office Action for U.S. Appl. No. 18/627,744, Dated Jan. 2, 2025, Fields, "Autonomous Vehicle Control Assessment and Selection," 29 pages.

(Continued)

*Primary Examiner* — Russell Frejd
(74) *Attorney, Agent, or Firm* — Lee & Hayes, P.C.

(57) ABSTRACT

Methods and systems for monitoring use, determining risk, and pricing insurance policies for a vehicle having one or more autonomous or semi-autonomous operation features are provided. According to certain aspects, the operating status of the features, the identity of a vehicle operator, risk levels for operation of the vehicle by the vehicle operator, or (Continued)

damage to the vehicle may be determined based upon sensor or other data. According to further aspects, decisions regarding transferring control between the features and the vehicle operator may be made based upon sensor data and information regarding the vehicle operator. Additional aspects may recommend or install updates to the autonomous operation features based upon determined risk levels. Some aspects may include monitoring transportation infrastructure and communicating information about the infrastructure to vehicles.

20 Claims, 14 Drawing Sheets

Related U.S. Application Data continuation of application No. 17/078,659, filed on Oct. 23, 2020, now Pat. No. 11,645,064, which is a continuation of application No. 15/935,556, filed on Mar. 26, 2018, now Pat. No. 10,831,191, which is a continuation of application No. 14/934,371, filed on Nov. 6, 2015, now Pat. No. 10,007,263.

(60) Provisional application No. 62/103,914, filed on Jan. 15, 2015, provisional application No. 62/103,911, filed on Jan. 15, 2015, provisional application No. 62/103,907, filed on Jan. 15, 2015, provisional application No. 62/103,895, filed on Jan. 15, 2015, provisional application No. 62/103,893, filed on Jan. 15, 2015, provisional application No. 62/103,891, filed on Jan. 15, 2015, provisional application No. 62/103,856, filed on Jan. 15, 2015, provisional application No. 62/103,855, filed on Jan. 15, 2015, provisional application No. 62/103,840, filed on Jan. 15, 2015, provisional application No. 62/103,838, filed on Jan. 15, 2015, provisional application No. 62/103,836, filed on Jan. 15, 2015, provisional application No. 62/103,831, filed on Jan. 15, 2015, provisional application No. 62/079,533, filed on Nov. 13, 2014.

(51) Int. Cl.

| | | |
|---|---|---|
| A61B 5/02 | (2006.01) | |
| B60K 35/00 | (2024.01) | |
| B60K 35/80 | (2024.01) | |
| B60K 35/85 | (2024.01) | |
| B60W 10/04 | (2006.01) | |
| B60W 30/06 | (2006.01) | |
| B60W 30/09 | (2012.01) | |
| B60W 30/095 | (2012.01) | |
| B60W 40/02 | (2006.01) | |
| B60W 40/08 | (2012.01) | |
| B60W 40/09 | (2012.01) | |
| B60W 50/02 | (2012.01) | |
| B60W 50/04 | (2006.01) | |
| B60W 50/08 | (2020.01) | |
| B60W 50/12 | (2012.01) | |
| B60W 50/14 | (2020.01) | |
| B60W 60/00 | (2020.01) | |
| B62D 15/02 | (2006.01) | |
| G01C 21/34 | (2006.01) | |
| G05D 1/00 | (2024.01) | |
| G05D 1/248 | (2024.01) | |
| G05D 1/617 | (2024.01) | |
| G06Q 30/0201 | (2023.01) | |

| | |
|---|---|
| G06Q 30/0207 | (2023.01) |
| G06Q 30/0217 | (2023.01) |
| G06Q 40/08 | (2012.01) |
| G07C 5/02 | (2006.01) |
| G07C 5/08 | (2006.01) |
| G08B 25/10 | (2006.01) |
| G08G 1/09 | (2006.01) |
| G08G 1/0962 | (2006.01) |
| G08G 1/14 | (2006.01) |
| B60W 50/00 | (2006.01) |

(52) U.S. Cl.
CPC .......... *A61B 5/4094* (2013.01); *A61B 5/6893* (2013.01); *A61B 5/7282* (2013.01); *B60K 35/00* (2013.01); *B60K 35/80* (2024.01); *B60K 35/85* (2024.01); *B60W 10/04* (2013.01); *B60W 30/06* (2013.01); *B60W 30/09* (2013.01); *B60W 30/0956* (2013.01); *B60W 40/02* (2013.01); *B60W 40/08* (2013.01); *B60W 40/09* (2013.01); *B60W 50/02* (2013.01); *B60W 50/0205* (2013.01); *B60W 50/045* (2013.01); *B60W 50/082* (2013.01); *B60W 50/12* (2013.01); *B60W 50/14* (2013.01); *B60W 60/0053* (2020.02); *B60W 60/0059* (2020.02); *B60W 60/007* (2020.02); *B62D 15/0285* (2013.01); *G01C 21/3407* (2013.01); *G05D 1/0055* (2013.01); *G05D 1/0214* (2013.01); *G05D 1/0278* (2013.01); *G05D 1/248* (2024.01); *G05D 1/617* (2024.01); *G06Q 30/0206* (2013.01); *G06Q 30/0207* (2013.01); *G06Q 30/0217* (2013.01); *G06Q 40/08* (2013.01); *G07C 5/02* (2013.01); *G07C 5/0808* (2013.01); *G08B 25/10* (2013.01); *G08G 1/091* (2013.01); *G08G 1/0962* (2013.01); *G08G 1/14* (2013.01); *B60W 2040/0809* (2013.01); *B60W 2040/0818* (2013.01); *B60W 2050/0071* (2013.01); *B60W 2050/0073* (2013.01); *B60W 2050/0075* (2013.01); *B60W 2050/0215* (2013.01); *B60W 2050/046* (2013.01); *B60W 2050/143* (2013.01); *B60W 2420/403* (2013.01); *B60W 2540/043* (2020.02); *B60W 2540/22* (2013.01); *B60W 2540/221* (2020.02); *B60W 2540/26* (2013.01); *B60W 2556/45* (2020.02); *B60W 2756/10* (2020.02); *B60W 2900/00* (2013.01)

(58) Field of Classification Search
CPC ...... A61B 5/7282; B60K 35/80; B60K 35/85; B60W 10/04; B60W 30/06; B60W 30/09; B60W 30/0956; B60W 40/02; B60W 40/08; B60W 40/09; B60W 50/02; B60W 50/0205; B60W 50/045; B60W 50/12; B60W 50/14; B60W 50/082; B60W 60/0059; B60W 60/0053; B60W 60/007; B60W 2040/0809; B60W 2040/0818; B60W 2050/0071; B60W 2050/0073; B60W 2050/0075; B60W 2050/0215; B60W 2050/046; B60W 2050/143; B60W 2420/403; B60W 2540/043; B60W 2540/22; B60W 2540/26; B60W 2540/221; B60W 2556/45; B60W 2900/00; B60W 2756/10; B62D 15/0285; G01C 21/3407; G05D 1/0055; G05D 1/0214; G05D 1/0278; G05D 1/248; G05D 1/617; G05D 2105/22; G05D 2105/31; G06Q 30/0206; G06Q 30/0207; G06Q 30/0217; G06Q 40/08; G07C 5/02;

G07C 5/0808; G08B 25/10; G08G 1/091;
G08G 1/0962; G08G 1/14
See application file for complete search history.

(56) References Cited

U.S. PATENT DOCUMENTS

| | | | |
|---|---|---|---|
| 8,698,639 B2 | 4/2014 | Fung et al. | |
| 8,818,608 B2 | 8/2014 | Cullinane et al. | |
| 8,874,301 B1 | 10/2014 | Rao et al. | |
| 9,063,543 B2 | 6/2015 | An et al. | |
| 9,075,413 B2 | 7/2015 | Cullinane et al. | |
| 9,098,080 B2 | 8/2015 | Norris et al. | |
| 9,235,211 B2 | 1/2016 | Davidsson et al. | |
| 9,342,074 B2 | 5/2016 | Dolgov et al. | |
| 9,352,752 B2 | 5/2016 | Cullinane et al. | |
| 9,390,452 B1 | 7/2016 | Biemer et al. | |
| 9,406,177 B2 | 8/2016 | Attard et al. | |
| 9,511,779 B2 | 12/2016 | Cullinane et al. | |
| 9,594,373 B2 | 3/2017 | Solyom et al. | |
| 9,830,748 B2 | 11/2017 | Rosenbaum | |
| 9,990,782 B2 | 6/2018 | Rosenbaum | |
| 10,269,190 B2 | 4/2019 | Rosenbaum | |
| 10,467,824 B2 | 11/2019 | Rosenbaum | |
| 10,657,597 B1 | 5/2020 | Billman et al. | |
| 10,783,587 B1 | 9/2020 | Augustine et al. | |
| 10,796,369 B1 | 10/2020 | Augustine et al. | |
| 10,915,965 B1 | 2/2021 | Fields et al. | |
| 11,040,726 B2 | 6/2021 | Tao et al. | |
| 11,227,452 B2 | 1/2022 | Rosenbaum | |
| 11,285,968 B2 | 3/2022 | Nguyen et al. | |
| 11,393,041 B1 | 7/2022 | Fields et al. | |
| 11,407,410 B2 | 8/2022 | Rosenbaum | |
| 11,524,707 B2 | 12/2022 | Rosenbaum | |
| 11,594,083 B1 | 2/2023 | Rosenbaum | |
| 11,685,402 B2 | 6/2023 | Lee et al. | |
| 11,720,968 B1 | 8/2023 | Fields et al. | |
| 12,086,583 B2 | 9/2024 | Fields et al. | |
| 2008/0161989 A1 | 7/2008 | Breed | |
| 2011/0241862 A1 | 10/2011 | Debouk et al. | |
| 2012/0028680 A1 | 2/2012 | Breed | |
| 2013/0131907 A1 | 5/2013 | Green et al. | |
| 2013/0231824 A1 | 9/2013 | Wilson et al. | |
| 2013/0265174 A1 | 10/2013 | Scofield et al. | |
| 2013/0267194 A1* | 10/2013 | Breed | G06V 10/143 |
| | | | 455/404.2 |
| 2013/0268187 A1 | 10/2013 | Scofield et al. | |
| 2013/0304513 A1 | 11/2013 | Hyde et al. | |
| 2013/0304514 A1 | 11/2013 | Hyde et al. | |
| 2014/0088814 A1 | 3/2014 | You et al. | |
| 2014/0148988 A1 | 5/2014 | Lathrop et al. | |
| 2014/0156133 A1 | 6/2014 | Cullinane et al. | |
| 2014/0156134 A1 | 6/2014 | Cullinane et al. | |
| 2014/0244096 A1 | 8/2014 | An et al. | |
| 2014/0303827 A1 | 10/2014 | Dolgov et al. | |
| 2014/0310186 A1 | 10/2014 | Ricci | |
| 2014/0330478 A1 | 11/2014 | Cullinane et al. | |
| 2014/0336935 A1 | 11/2014 | Zhu et al. | |
| 2014/0337816 A1 | 11/2014 | Chiluvuri | |
| 2015/0070160 A1 | 3/2015 | Davidsson et al. | |
| 2015/0170287 A1 | 6/2015 | Tirone et al. | |
| 2015/0187015 A1 | 7/2015 | Adams et al. | |
| 2015/0187019 A1 | 7/2015 | Fernandes et al. | |
| 2015/0193695 A1 | 7/2015 | Cruz Mota et al. | |
| 2015/0253772 A1 | 9/2015 | Solyom et al. | |
| 2015/0266488 A1 | 9/2015 | Solyom et al. | |
| 2015/0284009 A1 | 10/2015 | Cullinane et al. | |
| 2016/0042650 A1 | 2/2016 | Stenneth | |
| 2016/0068103 A1 | 3/2016 | McNew et al. | |
| 2016/0200326 A1 | 7/2016 | Cullinane et al. | |
| 2016/0272219 A1 | 9/2016 | Ketfi-Cherif et al. | |
| 2017/0023945 A1 | 1/2017 | Cavalcanti et al. | |
| 2017/0176641 A1 | 6/2017 | Zhu et al. | |
| 2017/0329346 A1 | 11/2017 | Latotzki | |
| 2018/0014182 A1 | 1/2018 | Jaegal et al. | |
| 2018/0194343 A1 | 7/2018 | Lorenz | |
| 2018/0233033 A1 | 8/2018 | Nordbruch | |
| 2019/0128408 A1 | 5/2019 | Kishi et al. | |
| 2020/0001891 A1 | 1/2020 | Takano et al. | |
| 2020/0164895 A1 | 5/2020 | Boss et al. | |
| 2020/0209875 A1 | 7/2020 | Marzani | |
| 2020/0211401 A1* | 7/2020 | Oshida | G05D 1/0295 |
| 2020/0342760 A1 | 10/2020 | Vassilovski et al. | |
| 2021/0094581 A1 | 4/2021 | Lee et al. | |
| 2021/0339773 A1 | 11/2021 | Lee et al. | |
| 2021/0403048 A1 | 12/2021 | Nguyen et al. | |
| 2022/0032963 A1 | 2/2022 | Gäng et al. | |
| 2022/0092893 A1 | 3/2022 | Rosenbaum | |
| 2022/0340148 A1 | 10/2022 | Rosenbaum | |
| 2023/0060300 A1 | 3/2023 | Rosenbaum | |
| 2023/0331261 A1 | 10/2023 | Oba | |
| 2024/0182083 A1 | 6/2024 | Zhu et al. | |
| 2024/0248708 A1 | 7/2024 | Fields et al. | |
| 2024/0256260 A1 | 8/2024 | Fields et al. | |
| 2024/0394038 A1 | 11/2024 | Fields | |
| 2026/0003604 A1 | 1/2026 | Fields | |

FOREIGN PATENT DOCUMENTS

| | | | |
|---|---|---|---|
| EP | 3730375 A1 | 4/2020 | |
| EP | 3960576 A1 | 3/2022 | |
| EP | 4190659 A1 | 6/2023 | |
| EP | 4190660 A1 | 6/2023 | |
| FR | 2705731 A1 | 12/1994 | |
| KR | 20060135757 A | 12/2006 | |

OTHER PUBLICATIONS

Office Action for U.S. Appl. No. 17/985,944, dated Feb. 10, 2025, 86 pages.
Office Action for U.S. Appl. No. 17/985,944, dated Sep. 26, 2024, Fields, "Autonomous Vehicle Operating Status Assessment," 68 pages.
Office Action for U.S. Appl. No. 17/985,944, dated Apr. 23, 2025, 46 Pages.
Office Action for U.S. Appl. No. 17/975,234, Dated May 8, 2025, Fields, "Autonomous Vehicle Automatic Parking," 11 pages.
Office Action for U.S. Appl. No. 17/985,944, dated Oct. 16, 2025, 40 pages.
An Evolving ITS Paves the Way for Intelligent Highways by Louis Frenzel, Electronic Design, Jan. 8, 2001 (Year: 2001), 14 pages.
Office Action for U.S. Appl. No. 18/627,143, dated Dec. 29, 2025, 12 pages.

* cited by examiner

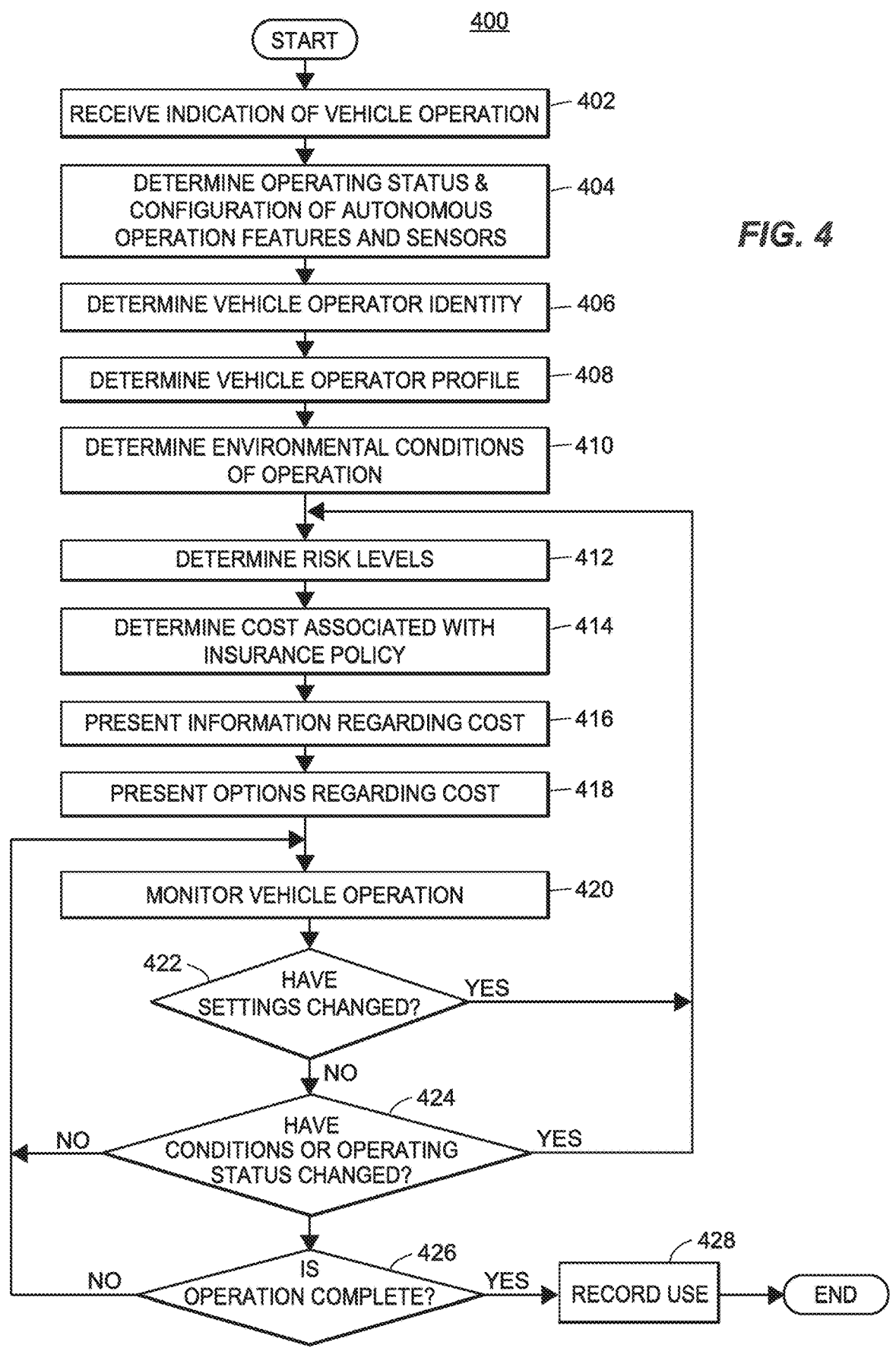

START

RECEIVE INDICATION OF VEHICLE OPERATION — 402

DETERMINE OPERATING STATUS & CONFIGURATION OF AUTONOMOUS OPERATION FEATURES AND SENSORS — 404

DETERMINE VEHICLE OPERATOR IDENTITY — 406

DETERMINE VEHICLE OPERATOR PROFILE — 408

DETERMINE ENVIRONMENTAL CONDITIONS OF OPERATION — 410

DETERMINE RISK LEVELS — 412

DETERMINE COST ASSOCIATED WITH INSURANCE POLICY — 414

PRESENT INFORMATION REGARDING COST — 416

PRESENT OPTIONS REGARDING COST — 418

MONITOR VEHICLE OPERATION — 420

422 — HAVE SETTINGS CHANGED?     YES

NO

424 — HAVE CONDITIONS OR OPERATING STATUS CHANGED?     YES

NO

NO     426 — IS OPERATION COMPLETE?     YES     RECORD USE — 428     END

500

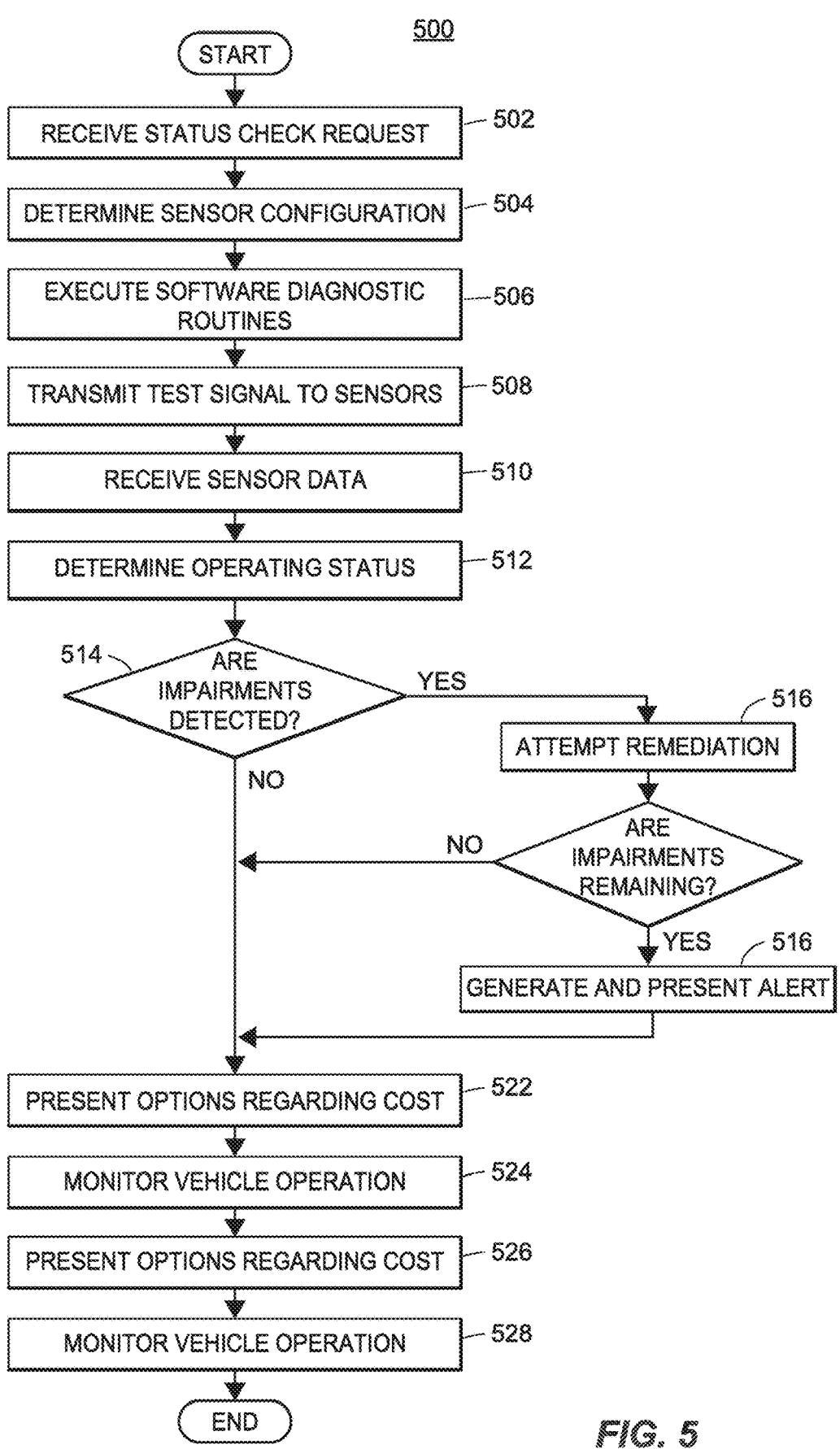

START

RECEIVE STATUS CHECK REQUEST —— 502

DETERMINE SENSOR CONFIGURATION —— 504

EXECUTE SOFTWARE DIAGNOSTIC ROUTINES —— 506

TRANSMIT TEST SIGNAL TO SENSORS —— 508

RECEIVE SENSOR DATA —— 510

DETERMINE OPERATING STATUS —— 512

514 —— ARE IMPAIRMENTS DETECTED?

YES

NO

ATTEMPT REMEDIATION —— 516

ARE IMPAIRMENTS REMAINING?

NO

YES —— 516

GENERATE AND PRESENT ALERT

PRESENT OPTIONS REGARDING COST —— 522

MONITOR VEHICLE OPERATION —— 524

PRESENT OPTIONS REGARDING COST —— 526

MONITOR VEHICLE OPERATION —— 528

END

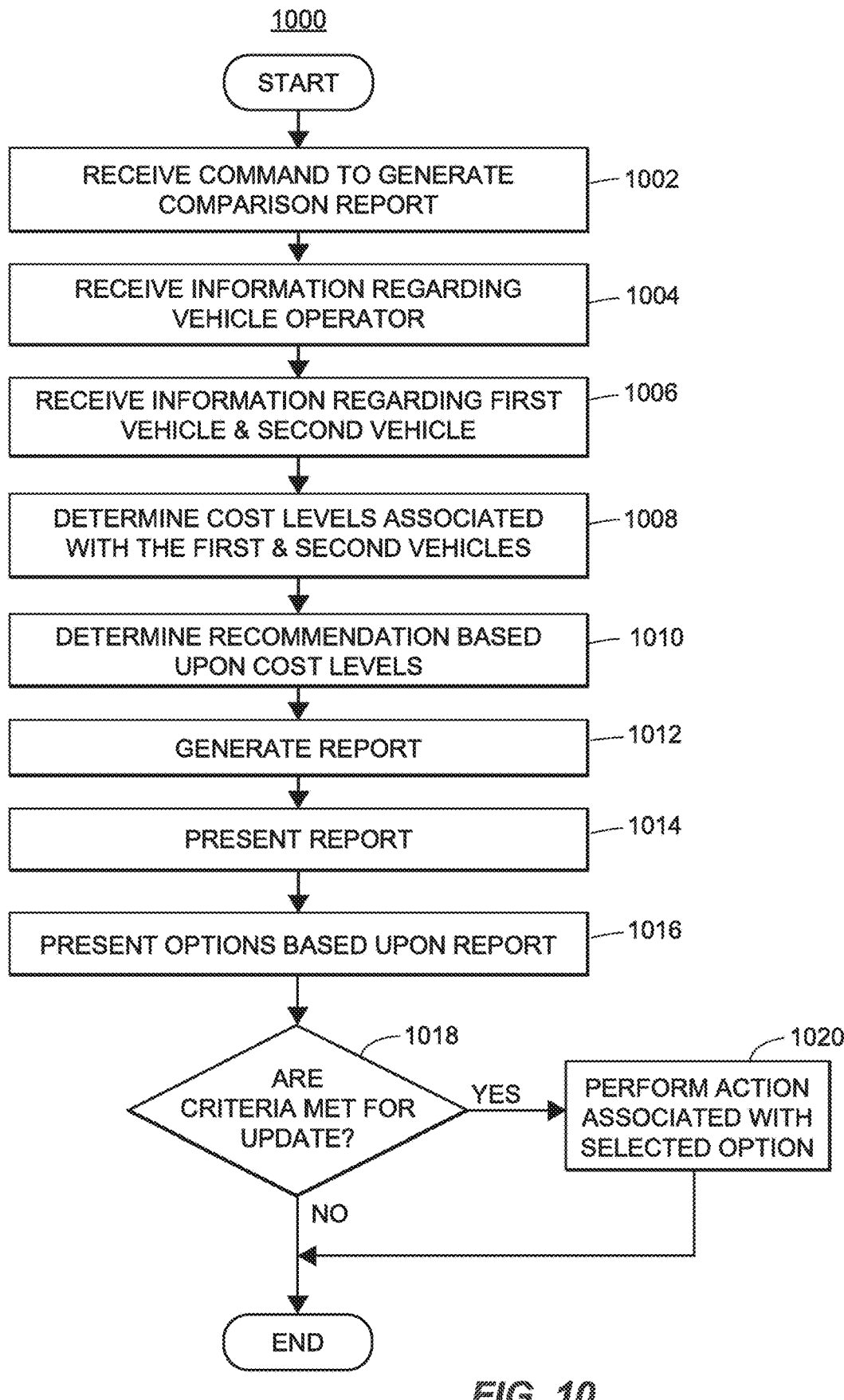

1000

START

RECEIVE COMMAND TO GENERATE COMPARISON REPORT — 1002

RECEIVE INFORMATION REGARDING VEHICLE OPERATOR — 1004

RECEIVE INFORMATION REGARDING FIRST VEHICLE & SECOND VEHICLE — 1006

DETERMINE COST LEVELS ASSOCIATED WITH THE FIRST & SECOND VEHICLES — 1008

DETERMINE RECOMMENDATION BASED UPON COST LEVELS — 1010

GENERATE REPORT — 1012

PRESENT REPORT — 1014

PRESENT OPTIONS BASED UPON REPORT — 1016

ARE CRITERIA MET FOR UPDATE? — 1018

YES → PERFORM ACTION ASSOCIATED WITH SELECTED OPTION — 1020

NO

END

FIG. 10

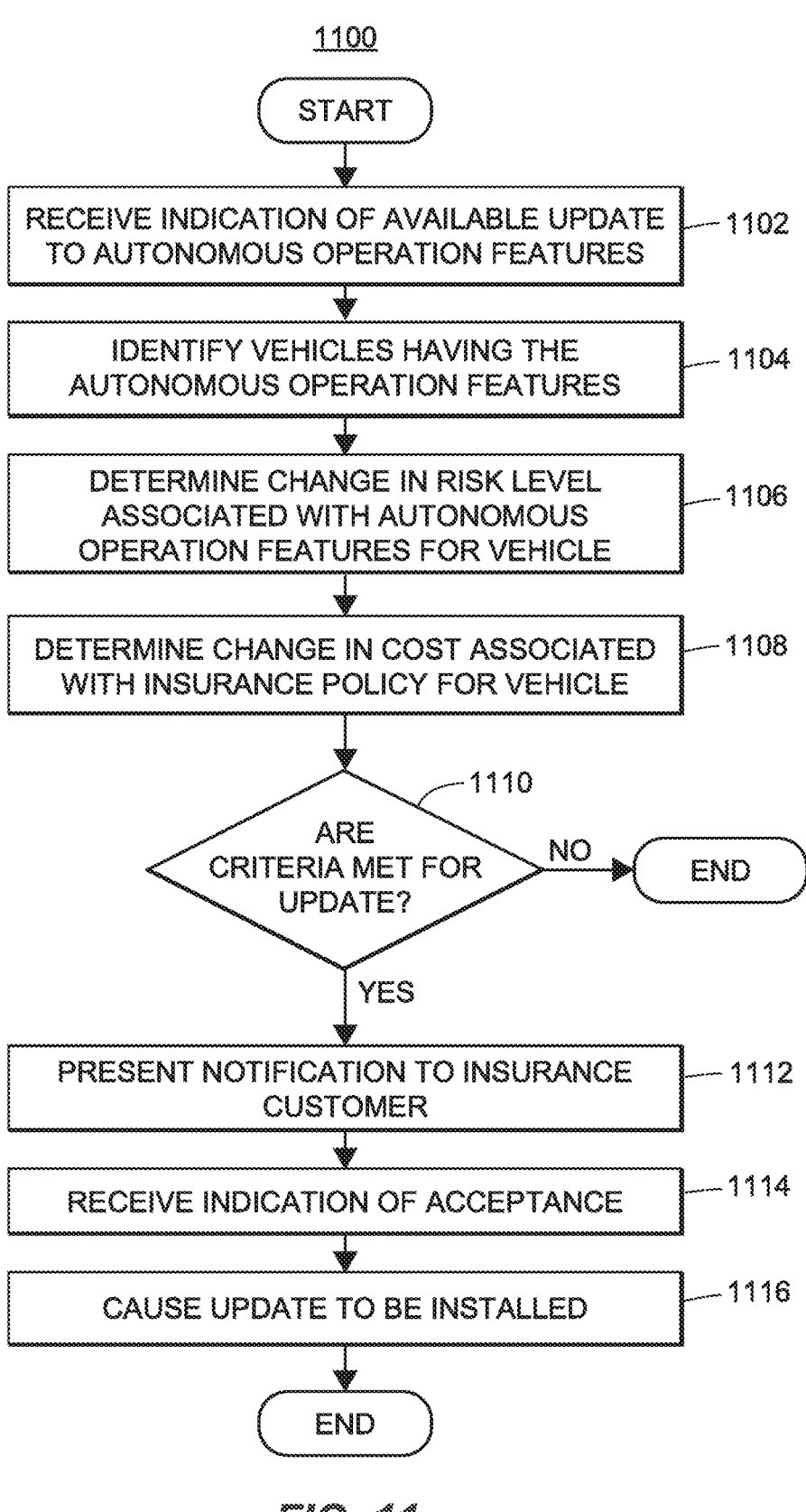

1100

START

RECEIVE INDICATION OF AVAILABLE UPDATE TO AUTONOMOUS OPERATION FEATURES — 1102

IDENTIFY VEHICLES HAVING THE AUTONOMOUS OPERATION FEATURES — 1104

DETERMINE CHANGE IN RISK LEVEL ASSOCIATED WITH AUTONOMOUS OPERATION FEATURES FOR VEHICLE — 1106

DETERMINE CHANGE IN COST ASSOCIATED WITH INSURANCE POLICY FOR VEHICLE — 1108

ARE CRITERIA MET FOR UPDATE? — 1110

NO → END

YES

PRESENT NOTIFICATION TO INSURANCE CUSTOMER — 1112

RECEIVE INDICATION OF ACCEPTANCE — 1114

CAUSE UPDATE TO BE INSTALLED — 1116

END

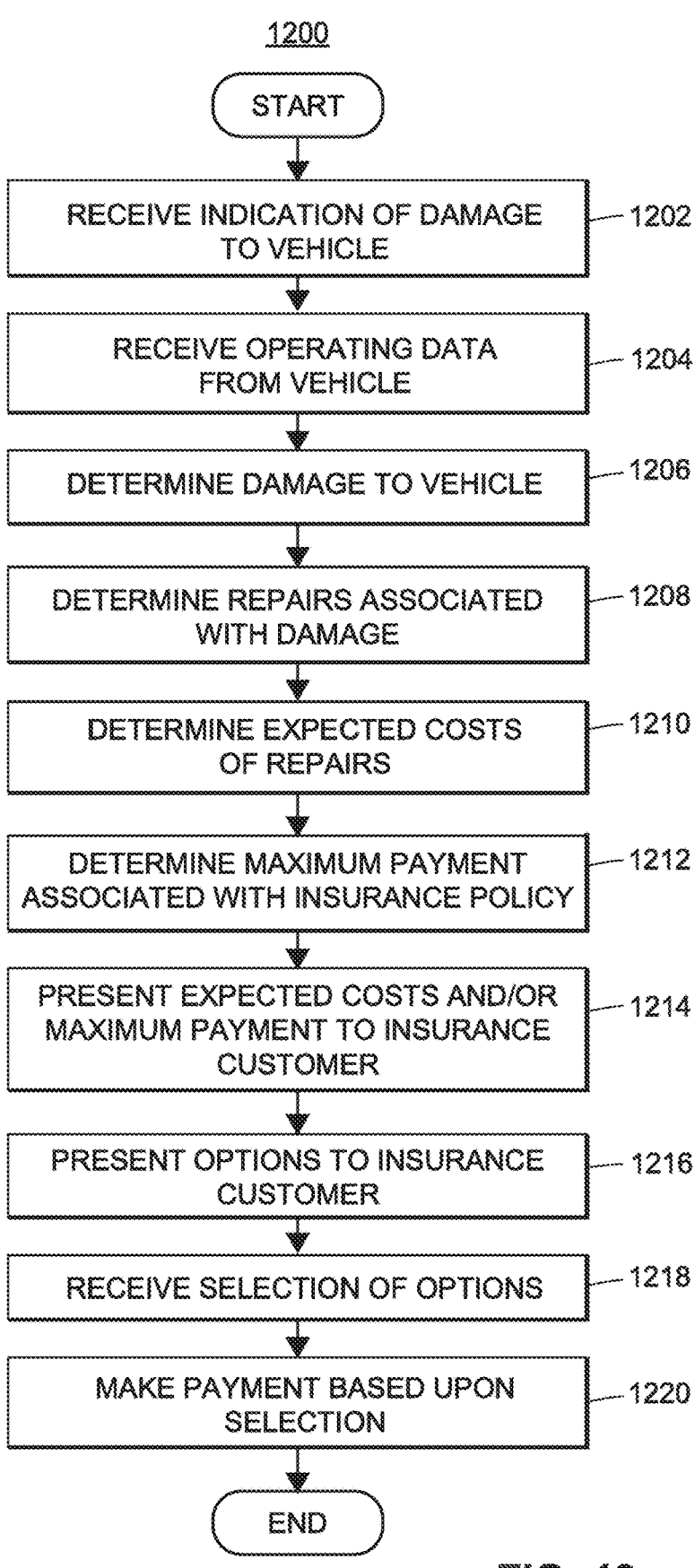

START

RECEIVE INDICATION OF DAMAGE TO VEHICLE —— 1202

RECEIVE OPERATING DATA FROM VEHICLE —— 1204

DETERMINE DAMAGE TO VEHICLE —— 1206

DETERMINE REPAIRS ASSOCIATED WITH DAMAGE —— 1208

DETERMINE EXPECTED COSTS OF REPAIRS —— 1210

DETERMINE MAXIMUM PAYMENT ASSOCIATED WITH INSURANCE POLICY —— 1212

PRESENT EXPECTED COSTS AND/OR MAXIMUM PAYMENT TO INSURANCE CUSTOMER —— 1214

PRESENT OPTIONS TO INSURANCE CUSTOMER —— 1216

RECEIVE SELECTION OF OPTIONS —— 1218

MAKE PAYMENT BASED UPON SELECTION —— 1220

END

START

RECEIVE SENSOR DATA REGARDING
INFRASTRUCTURE COMPONENT — 1302

DETERMINE MESSAGE BASED UPON
SENSOR DATA — 1304

ADD INDICATION OF SPONSOR
TO MESSAGE — 1306

ENCODE MESSAGE — 1308

TRANSMIT MESSAGE TO VEHICLE — 1310

CAUSE MESSAGE TO BE PRESENTED
TO VEHICLE OPERATOR — 1314

END

AUTONOMOUS VEHICLE ACCIDENT AND EMERGENCY RESPONSE

CROSS-REFERENCE TO RELATED APPLICATIONS

This application is a continuation of U.S. patent application Ser. No. 18/134,365 (filed Apr. 13, 2023), now U.S. Pat. No. 12,032,945, which is a continuation of U.S. Patent Application No. 17,078,659 (filed Oct. 23, 2020), now U.S. Pat. No. 11,645,064, which is a continuation of U.S. patent application Ser. No. 15/935,556 (filed Mar. 26, 2018), now U.S. Pat. No. 10,831,191, which is a continuation of U.S. patent application Ser. No. 14/934,371 (filed Nov. 6, 2015), now U.S. Pat. No. 10,007,263, which claims the benefit of U.S. Provisional Application No. 62/079,533 (filed Nov. 13, 2014); U.S. Provisional Application No. 62/103,831 (filed Jan. 15, 2015); U.S. Provisional Application No. 62/103,836 (filed Jan. 15, 2015); U.S. Provisional Application No. 62/103,838 (filed Jan. 15, 2015); U.S. Provisional Application No. 62/103,840 (filed Jan. 15, 2015); U.S. Provisional Application No. 62/103,855 (filed Jan. 15, 2015); U.S. Provisional Application No. 62/103,856 (filed Jan. 15, 2015); U.S. Provisional Application No. 62/103,891 (filed Jan. 15, 2015); U.S. Provisional Application No. 62/103,893 (filed Jan. 15, 2015); U.S. Provisional Application No. 62/103,895 (filed Jan. 15, 2015); U.S. Provisional Application No. 62/103,907 (filed Jan. 15, 2015); U.S. Provisional Application No. 62/103,911 (filed Jan. 15, 2015); and U.S. Provisional Application No. 62/103,914 (filed Jan. 15, 2015). The entirety of each of the foregoing applications is incorporated by reference herein.

Additionally, the present application is related to U.S. patent application Ser. No. 14/934,326 (filed Nov. 6, 2015); U.S. patent application Ser. No. 14/934,333 (filed Nov. 6, 2015); U.S. patent application Ser. No. 14/931,339 (filed Nov. 6, 2015); U.S. patent application Ser. No. 14/934,343 (filed Nov. 6, 2015); U.S. patent application Ser. No. 14/934,345 (filed Nov. 6, 2015); U.S. patent application Ser. No. 14/934,347 (filed Nov. 6, 2015); U.S. patent application Ser. No. 14/934,352 (filed Nov. 6, 2015); U.S. patent application Ser. No. 14/934,355 (filed Nov. 6, 2015); U.S. patent application Ser. No. 14/934,357 (filed Nov. 6, 2015); U.S. patent application Ser. No. 14/934,361 (filed Nov. 6, 2015); U.S. patent application Ser. No. 14/934,381 (filed Nov. 6, 2015); U.S. patent application Ser. No. 14/934,385 (filed Nov. 6, 2015); U.S. patent application Ser. No. 14/934,388 (filed Nov. 6, 2015); U.S. patent application Ser. No. 14/934,393 (filed Nov. 6, 2015); U.S. patent application Ser. No. 14/934,400 (filed Nov. 6, 2015); U.S. patent application Ser. No. 14/934,405 (filed Nov. 6, 2015); U.S. patent application Ser. No. 15/869,777 (filed Jan. 12, 2018); and U.S. patent application Ser. No. 15/895,533 (filed Feb. 13, 2018).

FIELD

The present disclosure generally relates to systems and methods for operating, monitoring, assessing, or insuring autonomous or semi-autonomous vehicles.

BACKGROUND

Vehicles are typically operated by a human vehicle operator who controls both steering and motive controls. Operator error, inattention, inexperience, misuse, or distraction leads to many vehicle accidents each year, resulting in injury and damage. Autonomous or semi-autonomous vehicles augment vehicle operators' information or replace vehicle operators' control commands to operate the vehicle in whole or part with computer systems based upon information from sensors within the vehicle.

Vehicle or automobile insurance exists to provide financial protection against physical damage and/or bodily injury resulting from traffic accidents and against liability that could arise therefrom. Typically, a customer purchases a vehicle insurance policy for a policy rate having a specified term. In exchange for payments from the insured customer, the insurer pays for damages to the insured which are caused by covered perils, acts, or events as specified by the language of the insurance policy. The payments from the insured are generally referred to as "premiums," and typically are paid on behalf of the insured over time at periodic intervals. An insurance policy may remain "in-force" while premium payments are made during the term or length of coverage of the policy as indicated in the policy. An insurance policy may "lapse" (or have a status or state of "lapsed"), for example, when premium payments are not being paid or if the insured or the insurer cancels the policy.

Premiums may be typically determined based upon a selected level of insurance coverage, location of vehicle operation, vehicle model, and characteristics or demographics of the vehicle operator. The characteristics of a vehicle operator that affect premiums may include age, years operating vehicles of the same class, prior incidents involving vehicle operation, and losses reported by the vehicle operator to the insurer or a previous insurer. Past and current premium determination methods do not, however, account for use of autonomous vehicle operating features. The present embodiments may, inter alia, alleviate this and/or other drawbacks associated with conventional techniques.

BRIEF SUMMARY

The present embodiments may be related to autonomous or semi-autonomous vehicle functionality, including driverless operation, accident avoidance, or collision warning systems. These autonomous vehicle operation features may either assist the vehicle operator to more safely or efficiently operate a vehicle or may take full control of vehicle operation under some or all circumstances. The present embodiments may also facilitate risk assessment and premium determination for vehicle insurance policies covering vehicles with autonomous operation features. For instance, a consumer may opt-in to a rewards program that rewards them, such as in the form of insurance discounts, for affirmatively sharing data related to their vehicles and/or autonomous features with an insurance provider.

In accordance with the described embodiments, the disclosure herein generally addresses systems and methods for directing a route of an autonomous or semi-autonomous vehicle during an emergency. A computer associated with the vehicle (such as an on-board computer, mobile device, or server communicatively connected to the vehicle) may (1) detect that an occupant of the vehicle is experiencing a medical emergency; (2) generate an indication of the detected medical emergency; (3) determine a vehicle location of the vehicle; (4) identify a medical facility based upon the vehicle location and the indication of the detected medical emergency; (5) determine one or more routes from the vehicle location to the medical facility; and/or (6) cause the vehicle to automatically travel to a medical facility along the determined one or more routes. The vehicle may be controlled by one or more autonomous operation features during travel along the determined one or more routes.

Causing the vehicle to automatically travel to the medical facility may include causing the one or more autonomous operation features to engage, causing the one or more autonomous operation features to control the operation of the vehicle along the determined one or more routes to the medical facility, and/or causing the vehicle to park at an appropriate location upon arrival at the medical facility. The autonomous operation features controlling the vehicle during travel may include the following: steering, accelerating, braking, parking, pedestrian detection, artificial intelligence, vehicle navigation, vehicle positioning, and/or remote vehicle location determination.

Some embodiment may further include communicating a message to one or more of the medical facility, a police department, a fire department, and/or a family member of the occupant. Such message may include a current location of the autonomous or semi-autonomous vehicle, the determined one or more routes to the medical facility, an estimated time of arrival of the autonomous or semi-autonomous vehicle at the medical facility, and/or information regarding the detected medical emergency.

In further embodiments, the medical emergency may be detected by a biometric device within the vehicle. The detected medical emergency may include one or more of a heart attack, a stroke, and/or a seizure. The vehicle location may be determined using a Global Positioning System (GPS) receiver.

In each of the embodiments or aspects described above, the methods may be provided in corresponding computer systems including at least one or more processors and a non-transitory program memory coupled to the one or more processors and storing executable instructions. The computer systems may further include or be communicatively connected to one or more sensors, communication con1ponents or devices, or other equipment as described herein. In yet another aspect, a tangible, non-transitory computer-readable medium storing instructions corresponding to each of the embodiments or aspects described above may be provided. Each of the methods or executable instructions of the computer systems or computer readable media may include additional, fewer, or alternate actions, including those discussed elsewhere herein.

BRIEF DESCRIPTION OF THE DRAWINGS

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

The figures described below depict various aspects of the applications, methods, and systems disclosed herein. It should be understood that each figure depicts an embodiment of a particular aspect of the disclosed applications, systems and methods, and that each of the figures is intended to accord with a possible embodiment thereof. Furthermore, wherever possible, the following description refers to the reference numerals included in the following figures, in which features depicted in multiple figures are designated with consistent reference numerals.

FIG. 4 illustrates a flow diagram of an exemplary monitoring method during vehicle operation in accordance with the presently described embodiments;

FIG. 5 illustrates a flow diagram of an exemplary operating status assessment method in accordance with the presently described embodiments;

FIG. 10 illustrates a flow diagram depicting an exemplary cost comparison method in accordance with the presently described embodiments; and FIG. 11 illustrates a flow diagram depicting an exemplary autonomous operation feature update method in accordance with the presently described embodiments;

FIG. 12 illustrates a flow diagram depicting an exemplary autonomous vehicle repair method in accordance with the presently described embodiments.

DETAILED DESCRIPTION

Figure 1:
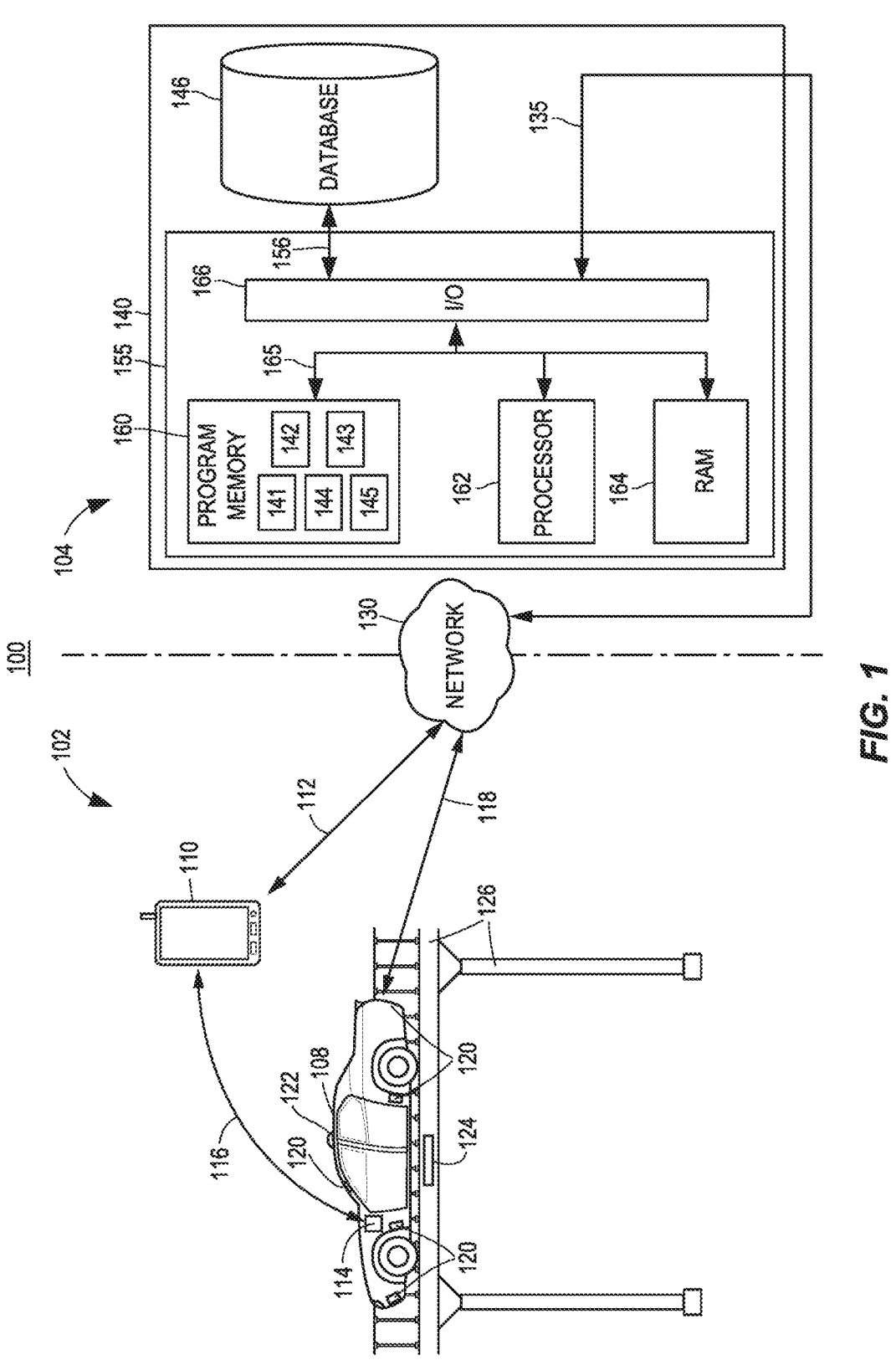
FIG. 1 illustrates a block diagram of an exemplary computer network, a computer server, a mobile device, and an on-board computer for implementing autonomous vehicle operation, monitoring, evaluation, and insurance processes in accordance with the described embodiments.

The systems and methods disclosed herein generally relate to evaluating, monitoring, and managing risks related to the operation of autonomous or semi-autonomous vehicles having autonomous (or semi-autonomous) operation features. The systems and methods further relate to pricing and processing vehicle insurance policies for autonomous or semi-autonomous vehicles. The autonomous operation features may take full control of the vehicle under certain conditions, viz. fully autonomous operation, or the autonomous operation features may assist the vehicle operator in operating the vehicle, viz. partially autonomous operation. Fully autonomous operation features may include systems within the vehicle that pilot the vehicle to a destination with or without a vehicle operator present (e.g., an operating system for a driverless car). Partially autonomous operation features may assist the vehicle operator in limited ways (e.g., automatic braking or collision avoidance systems).

The type and quality of the autonomous operation features may affect the risks related to operating a vehicle, both individually and/or in combination. In addition, configurations and settings of the autonomous operation features may further impact the risks. To account for the effects on such risks, some embodiments evaluate the quality of each autonomous operation feature and/or combination of features. Additional embodiments evaluate the risks associated with the vehicle operator interacting with the autonomous operation features. Further embodiments address the relative risks associated with control of some aspects of vehicle control by the autonomous operation features or by the vehicle operator. Still further embodiments address use of information received or generated by the autonomous operation features to manage risk and/or damage.

Some autonomous operation features may be adapted for use under particular conditions, such as city driving or highway driving. Additionally, the vehicle operator may be able to configure settings relating to the features or may enable or disable the features individually or in groups. For example, the vehicle operator may select a mode of operation for the autonomous or semi-autonomous vehicle, which may adjust settings for one or more autonomous operation features. Therefore, some embodiments monitor use of the autonomous operation features, which may include the settings or levels of feature use during vehicle operation, as well as the selection of features or settings of the autonomous operation features chosen by the vehicle operator.

Information obtained by monitoring feature usage may be used to determine risk levels associated with vehicle operation, either generally or in relation to a vehicle operator. In such situations, total risk may be determined by a weighted combination of the risk levels associated with operation while autonomous operation features are enabled (with relevant settings) and the risk levels associated with operation while autonomous operation features are disabled. For fully autonomous vehicles, settings or configurations relating to vehicle operation may be monitored and used in determining vehicle operating risk.

In addition to use in controlling the vehicle, information regarding the risks associated with vehicle operation with and without the autonomous operation features may then be used to determine risk categories or premiums for a vehicle insurance policy covering a vehicle with autonomous operation features. Risk category or price may be determined based upon factors relating to the evaluated effectiveness of the autonomous vehicle features. The risk or price determination may also include traditional factors, such as location, vehicle type, and level of vehicle use. For fully autonomous vehicles, factors relating to vehicle operators may be excluded entirely. For partially autonomous vehicles, factors relating to vehicle operators may be reduced in proportion to the evaluated effectiveness and monitored usage levels of the autonomous operation features. For vehicles with autonomous communication features that obtain information from external sources (e.g., other vehicles or infrastructure), the risk level and/or price determination may also include an assessment of the availability of external sources of information. Location and/or timing of vehicle use may thus be monitored and/or weighted to determine the risk associated with operation of the vehicle.

Autonomous Automobile Insurance

The present embodiments may relate to assessing and pricing insurance based upon autonomous (or semi-autonomous) functionality of a vehicle, utilization of the autonomous (or semi-autonomous) functionality of the vehicle, and/or operation of the vehicle by a human operator. In some embodiments, the vehicle operator may not control the operations of the vehicle directly, in which case the assessment, rating, and pricing of insurance may exclude consideration of the vehicle operator. A smart vehicle may maneuver itself without human intervention and/or include sensors, processors, computer instructions, and/or other components that may pe1form or direct ce1iain actions conventionally performed by a human operator.

An analysis of how artificial intelligence facilitates avoiding accidents and/or mitigates the severity of accidents may be used to build a database and/or model of risk assessment. After which, automobile insurance risk and/or premiums (as well as insurance discounts, rewards, and/or points) may be adjusted based upon autonomous or semi-autonomous vehicle functionality, such as by groups of autonomous or semi-autonomous functionality or individual features. In one aspect, an evaluation may be performed on how artificial intelligence, and the usage thereof, impacts automobile accidents and/or automobile insurance claims.

The types of autonomous or semi-autonomous vehicle-related functionality or technology that may be used with the present embodiments to replace human driver actions may include and/or be related to the following types of functionality: (a) fully autonomous (driverless); (b) limited driver control; (c) vehicle-to-vehicle (V2V) wireless communication; (d) vehicle-to-infrastructure (and/or vice versa) wireless communication; (c) automatic or semiautomatic steering; (f) automatic or semi-automatic acceleration; (g) automatic or semiautomatic braking; (h) automatic or semi-automatic blind spot monitoring; (i) automatic or semiautomatic collision warning; (j) adaptive cruise control; (k) automatic or semi-automatic parking/parking assistance; (l) automatic or semi-automatic collision preparation (windows roll up, seat adjusts upright, brakes pre-charge, etc.); (m) driver acuity/alertness monitoring; (n) pedestrian detection; (o) autonomous or semi-autonomous backup systems; (p) road mapping systems; (q) software security and anti-hacking measures; (r) theft prevention/automatic return; (s) automatic or semi-automatic driving without occupants; and/or other functionality. Additionally or alternatively, the autonomous or semi-autonomous functionality or technology may include and/or may be related to: (t) driver alertness or responsive monitoring; (u) pedestrian detection; (v) artificial intelligence and/or back-up systems; (w) navigation or GPS-related systems; (x) security and/or anti-hacking measures; and/or (y) theft prevention systems.

The adjustments to automobile insurance rates or premiums based upon the autonomous or semi-autonomous vehicle-related functionality or technology may take into account the impact of such functionality or technology on the likelihood of a vehicle accident or collision occurring. For instance, a processor may analyze historical accident information and/or test data involving vehicles having autonomous or semi-autonomous functionality. Factors that may be analyzed and/or accounted for that are related to insurance risk, accident information, or test data may include (1) point of impact; (2) type of road; (3) time of day; (4) weather conditions; (5) road construction; (6) type/length of trip; (7) vehicle style; (8) level of pedestrian traffic; (9) level of vehicle congestion; (10) atypical situations (such as manual traffic signaling); (11) availability of internet connection for the vehicle; and/or other factors. These types of factors may also be weighted according to historical accident information, predicted accidents, vehicle trends, test data, and/or other considerations.

In one aspect, the benefit of one or more autonomous or semi-autonomous functionalities or capabilities may be determined, weighted, and/or otherwise characterized. For instance, the benefit of certain autonomous or semi-autonomous functionality may be substantially greater in city or congested traffic, as compared to open road or country driving traffic. Additionally or alternatively, certain autonomous or semi-autonomous functionality may only work effectively below a certain speed, e.g., during city driving or driving in congestion. Other autonomous or semi-autonomous functionality may operate more effectively on the highway and away from city traffic, such as cruise control. Further individual autonomous or semi-autonomous functionality may be impacted by weather, such as rain or snow, and/or time of day (day light versus night). As an example, fully automatic or semi-automatic lane detection warnings may be impacted by rain, snow, ice, and/or the amount of sunlight (all of which may impact the imaging or visibility of lane markings painted onto a road surface, and/or road markers or street signs).

Automobile insurance premiums, rates, discounts, rewards, refunds, points, or other costs may be adjusted based upon the percentage of time or vehicle usage that the vehicle is the driver, i.e., the amount of time a specific driver uses each type of autonomous (or even semiautonomous) vehicle functionality. Such premiums, rates, discounts, rewards, refunds, points, or other costs may further be adjusted based upon the extent of use of the autonomous operation features, including settings or modes impacting the operation of the autonomous operation features. Moreover, information regarding the vehicle environment during use (e.g., weather, traffic, time of day, etc.) may be included in insurance adjustment determinations, as may traditional information regarding one or more vehicle operators (and the extent to which each vehicle operator uses the vehicle).

Such usage information for a particular vehicle may be gathered over time and/or via remote wireless communication with the vehicle. One embodiment may involve a processor on the vehicle, such as within a vehicle control system or dashboard, monitoring in real-time the vehicle operator and/or the use of autonomous operation features while the vehicle is operating. Other types of monitoring may be remotely performed, such as via wireless communication between the vehicle and a remote server, or wireless communication between a vehicle-mounted dedicated device (that is configured to gather autonomous or semi-autonomous functionality usage information) and a remote server.

Additionally, in some embodiments, the vehicle may transmit and/or receive communications to or from external sources, such as other vehicles (V2V), infrastructure (e.g., a bridge, traffic light, railroad crossing, toll both, marker, sign, or other equipment along the side of a road or highway), pedestrians, databases, or other information sources external to the vehicle. Such communication may allow the vehicle to obtain information regarding other vehicles, obstacles, road conditions, or environmental conditions that could not be detected by sensors disposed within the vehicle. For example, V2V communication may allow a vehicle to identify other vehicles approaching an intersection even when the direct line between the vehicle and the other vehicles is obscured by buildings. As another example, the V2V wireless communication from a first vehicle to a second vehicle (following the first vehicle) may indicate that the first vehicle is braking, which may include the degree to which the vehicle is braking. In response, the second vehicle may automatically or autonomously brake in advance of detecting the deceleration of the first vehicle based upon sensor data.

Insurance premiums, rates, ratings, discounts, rewards, special offers, points, programs, refunds, claims, claim amounts, or other costs associated with an insurance policy may be adjusted for, or may otherwise take into account, the foregoing functionality and/or the other functionality described herein. For instance, insurance policies may be updated based upon installed autonomous operation features, the extent of use of the autonomous operation features, V2V wireless communication, and/or vehicle-to-infrastructure or infrastructure-to-vehicle wireless communication. The present embodiments may assess and price insurance risks at least in part based upon autonomous operation features that replace some actions of the vehicle operator in controlling the vehicle, including settings and operating status of the autonomous operation features.

Exemplary Autonomous Vehicle Operation System

FIG. 1 illustrates a block diagram of an exemplary autonomous vehicle insurance system 100 on which the exemplary methods described herein may be implemented. The high-level architecture includes both hardware and software applications, as well as various data communications channels for communicating data between the various hardware and software components. The autonomous vehicle insurance system 100 may be roughly divided into frontend components 102 and back-end components 104. The front-end components 102 may obtain information regarding a vehicle 108 (e.g., a car, truck, motorcycle, etc.) and the surrounding environment. An on-board computer 114 may utilize this information to operate the vehicle 108 according to an autonomous operation feature or to assist the vehicle operator in operating the vehicle 108. To monitor the vehicle 108, the front-end components 102 may include one or more sensors 120 installed within the vehicle 108 that may communicate with the on-board computer 114. The front-end components 102 may further process the sensor data using the onboard computer 114 or a mobile device 110 (e.g., a smart phone, a tablet computer, a special purpose computing device, etc.) to determine when the vehicle is in operation and information regarding the vehicle. In some embodiments of the system 100, the front-end components 102 may communicate with the back-end components 104 via a network 130. Either the on-board computer 114 or the mobile device 110 may communicate with the back-end components 104 via the network 130 to allow the back-end components 104 to record information regarding vehicle usage. The back-end components 104 may use one or more servers 140 to receive data from the front-end components 102, determine use and effectiveness of autonomous operation features, determine risk levels or premium price, and/or facilitate purchase or renewal of an autonomous vehicle insurance policy.

The front-end components 102 may be disposed within or communicatively connected to one or more on-board computers 114, which may be permanently or removably installed in the vehicle 108. The on-board computer 114 may interface with the one or more sensors 120 within the vehicle 108 (e.g., an ignition sensor, an odometer, a system clock, a speedometer, a tachometer, an accelerometer, a gyroscope, a compass, a geolocation unit, a camera, a distance sensor, etc.), which sensors may also be incorporated within or connected to the on-board computer 114. The front-end components 102 may further include a communication component 122 to transmit information to and receive information from external sources, including other vehicles, infrastructure, or the back-end components 104. In some embodiments, the mobile device 110 may supplement the functions performed by the on-board computer 114 described herein by, for example, sending or receiving information to and from the mobile server 140 via the network 130. In other embodiments, the on-board computer 114 may perform all of the functions of the mobile device 110 described herein, in which case no mobile device 110 may be present in the system 100. Either or both of the mobile device 110 or on-board computer 114 may communicate with the network 130 over links 112 and 118, respectively. Additionally, the mobile device 110 and on-board computer 114 may communicate with one another directly over link 116.

The mobile device 110 may be either a general-use personal computer, cellular phone, smart phone, tablet computer, phablet, wearable electronics, PDA (personal digital assistant), smart glasses, smart watches, smart bracelet, pager, computing device configured for wired or wireless RF (radio frequency) communication, a dedicated vehicle use monitoring device, and/or other mobile computing device. Although only one mobile device 110 is illustrated, it should be understood that a plurality of mobile devices 110 may be used in some embodiments. The on-board computer 114 may be a general-use on-board computer capable of performing many functions relating to vehicle operation or a dedicated computer for autonomous vehicle operation. Further, the on-board computer 114 may be installed by the manufacturer of the vehicle 108 or as an aftermarket modification or addition to the vehicle 108. In some embodiments or under certain conditions, the mobile device 110 or on-board computer 114 may function as thin-client devices that outsource some or most of the processing to the server 140.

The sensors 120 may be removably or fixedly installed within the vehicle 108 and may be disposed in various arrangements to provide information to the autonomous operation features. Among the sensors 120 may be included one or more of a GPS (Global Positioning System) unit, other satellite-based navigation unit, a radar unit, a LID AR (Light Detection and Ranging) unit, an ultrasonic sensor, an infrared sensor, a camera, an accelerometer, a tachometer, and/or a speedometer. Some of the sensors 120 (e.g., radar, LIDAR, or camera units) may actively or passively scan the vehicle environment for obstacles (e.g., other vehicles, buildings, pedestrians, etc.), lane markings, or signs or signals. Other sensors 120 (e.g., GPS, accelerometer, or tachometer units) may provide data for determining the location or movement of the vehicle 108. Other sensors 120 may be directed to the interior or passenger compartment of the vehicle 108, such as cameras, microphones, pressure sensors, thermometers, or similar sensors to monitor the vehicle operator and/or passengers within the vehicle 108. Information generated or received by the sensors 120 may be communicated to the on-board computer 114 or the mobile device 110 for use in autonomous vehicle operation.

In some embodiments, the communication component 122 may receive information from external sources, such as other vehicles or infrastructure. The communication component 122 may also send information regarding the vehicle 108 to external sources. To send and receive information, the communication component 122 may include a transmitter and a receiver designed to operate according to predetermined specifications, such as the dedicated short-range communication (DSRC) channel, wireless telephony, Wi-Fi, or other existing or later-developed communications protocols. The received information may supplement the data received from the sensors 120 to implement the autonomous operation features. For example, the communication component 122 may receive information that an autonomous vehicle ahead of the vehicle 108 is reducing speed, allowing the adjustments in the autonomous operation of the vehicle 108.

In further embodiments, the front-end components may include an infrastructure communication device 124 for monitoring the status of one or more infrastructure components 126. The infrastructure communication device 124 may include or be communicatively connected to one or more sensors (not shown) for detecting information relating to the condition of the infrastructure component 126. The sensors (not shown) may generate data relating to weather conditions, traffic conditions, or operating status of the infrastructure component 126. The infrastructure communication device 124 may be configured to receive the sensor data generated and determine a condition of the infrastructure component 126, such as weather conditions, road integrity, construction, traffic, available parking spaces, etc. The infrastructure communication device 124 may further be configured to communicate information to vehicles 108 via the communication component 122. In some embodiments, the infrastructure communication device 124 may receive information from the vehicles 108, while, in other embodiments, the infrastructure communication device 124 may only transmit information to the vehicles 108.

In addition to receiving information from the sensors 120, the on-board computer 114 may directly or indirectly control the operation of the vehicle 108 according to various autonomous operation features. The autonomous operation features may include software applications or routines implemented by the on-board computer 114 to control the steering, braking, or throttle of the vehicle 108. To facilitate such control, the on-board computer 114 may be communicatively connected to the controls or components of the vehicle 108 by various electrical or electromechanical control components (not shown). In embodiments involving fully autonomous vehicles, the vehicle 108 may be operable only through such control components (not shown). In other embodiments, the control components may be disposed within or supplement other vehicle operator control components (not shown), such as steering wheels, accelerator or brake pedals, or ignition switches.

In some embodiments, the front-end components 102 may communicate with the back-end components 104 via the network 130. The network 130 may be a proprietary network, a secure public internet, a virtual private network or some other type of network, such as dedicated access lines, plain ordinary telephone lines, satellite links, cellular data networks, combinations of these. Where the network 130 comprises the Internet, data communications may take place over the network 130 via an Internet communication protocol.

The back-end components 104 may include one or more servers 140. Each server 140 may include one or more computer processors adapted and configured to execute various software applications and components of the autonomous vehicle insurance system 100, in addition to other software applications. The server 140 may further include a database 146, which may be adapted to store data related to the operation of the vehicle 108 and its autonomous operation features. Such data might include, for example, dates and times of vehicle use, duration of vehicle use, use and settings of autonomous operation features, speed of the vehicle 108, RPM or other tachometer readings of the vehicle 108, lateral and longitudinal acceleration of the vehicle 108, incidents or near collisions of the vehicle 108, communication between the autonomous operation features and external sources, environmental conditions of vehicle operation (e.g., weather, traffic, road condition, etc.), errors or failures of autonomous operation features, or other data relating to use of the vehicle 108 and the autonomous operation features, which may be uploaded to the server 140 via the network 130. The server 140 may access data stored in the database 146 when executing various functions and tasks associated with the evaluating feature effectiveness or assessing risk relating to an autonomous vehicle.

Although the autonomous vehicle insurance system 100 is shown to include one vehicle 108, one mobile device 110, one on-board computer 114, and one server 140, it should be understood that different numbers of vehicles 108, mobile devices 110, on-board computers 114, and/or servers 140 may be utilized. For example, the system 100 may include a plurality of servers 140 and hundreds of mobile devices 110 or on-board computers 114, all of which may be interconnected via the network 130. Furthermore, the database storage or processing performed by the one or more servers 140 may be distributed among a plurality of servers 140 in an arrangement known as "cloud computing." This configuration may provide various advantages, such as enabling near real-time uploads and downloads of information as well as periodic uploads and downloads of information. This may in turn support a thin-client embodiment of the mobile device 110 or on-board computer 114 discussed herein.

The server 140 may have a controller 155 that is operatively connected to the database 146 via a link 156. It should be noted that, while not shown, additional databases may be linked to the controller 155 in a known manner. For example, separate databases may be used for autonomous operation feature information, vehicle insurance policy information, and vehicle use information. The controller 155 may include a program memory 160, a processor 162 (which may be called a microcontroller or a microprocessor), a random-access memory (RAM) 164, and an input/output (I/O) circuit 166, all of which may be interconnected via an address/data bus 165. It should be appreciated that although only one microprocessor 162 is shown, the controller 155 may include multiple microprocessors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM 164 and program memories 160 may be implemented as semiconductor memories, magnetically readable memories, or optically readable memories, for example. The controller 155 may also be operatively connected to the network 130 via a link 135.

The server 140 may further include a number of software applications stored in a program memory 160. The various software applications on the server 140 may include an autonomous operation information monitoring application 141 for receiving information regarding the vehicle 108 and its autonomous operation features, a feature evaluation application 142 for determining the effectiveness of autonomous operation features under various conditions, a compatibility evaluation application 143 for determining the effectiveness of combinations of autonomous operation features, a risk assessment application 144 for determining a risk category associated with an insurance policy covering an autonomous vehicle, and an autonomous vehicle insurance policy purchase application 145 for offering and facilitating purchase or renewal of an insurance policy covering an autonomous vehicle. The various software applications may be executed on the same computer processor or on different computer processors.

The various software applications may include various software routines stored in the program memory 160 to implement various modules using the process 162. Additionally, or alternatively, the software applications or routines may interact with various hardware modules that may be installed within or connected to the server 140. Such modules may implement part of all of the various exemplary methods discussed herein or other related embodiments. Such modules may include a vehicle control module for determining and implementing control decisions to operate the vehicle 108, a system status module for determining the operating status of autonomous operation features, a monitoring module for monitoring the operation of the vehicle 108, a remediation module for correcting abnormal operating states of autonomous operation features, an insurance module for determining risks and costs associated with operation of the vehicle 108, an alert module for generating and presenting alerts regarding the vehicle 108 or the vehicle operator, a risk assessment module for determining risks associated with operation of the vehicle 108 by the autonomous operation features or by the vehicle operator, an identification module for identifying or verifying the identity of the vehicle operator, an information module for obtaining information regarding a vehicle operator or vehicle 108, a use cost module for determining costs associated with operation of the vehicle 108, a comparison module for comparing one or more costs associated with owning or operating the vehicle 108, an update module for updating an autonomous operation feature of the vehicle 108, or other modules.

Exemplary Mobile Device or On-Board Computer

Figure 2:
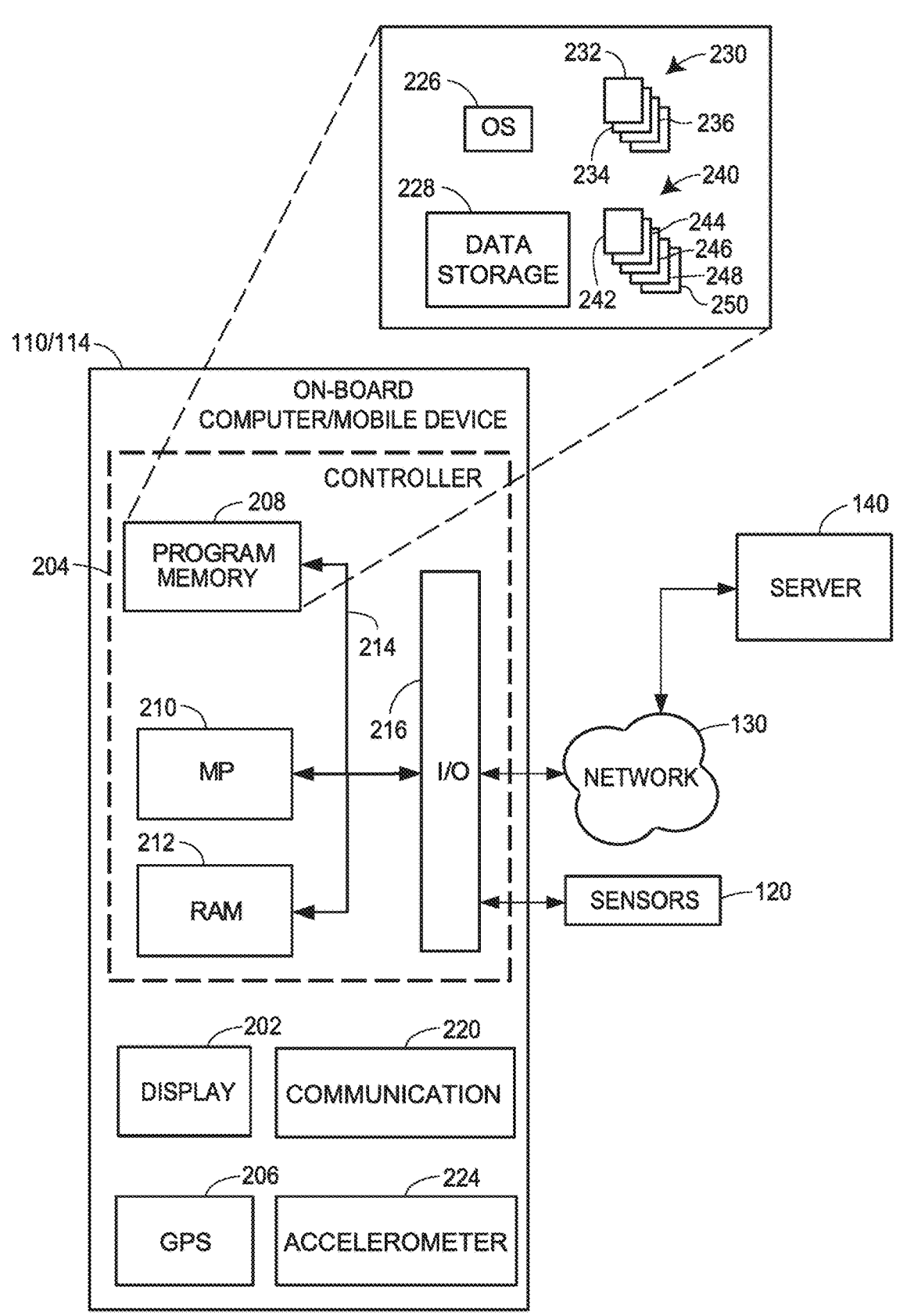
FIG. 2 illustrates a block diagram of an exemplary onboard computer or mobile device.

FIG. 2 illustrates a block diagram of an exemplary mobile device 110 and/or an exemplary on-board computer 114 consistent with the system 100. The mobile device 110 and/or on-board computer 114 may include a display 202, a GPS unit 206, a communication unit 220, an accelerometer 224, one or more additional sensors (not shown), a user-input device (not shown), and/or, like the server 140, a controller 204. In some embodiments, the mobile device 110 and on-board computer 114 may be integrated into a single device, or either may perform the functions of both. The on-board computer 114 (or mobile device 110) may interface with the sensors 120 to receive information regarding the vehicle 108 and its environment, which information may be used by the autonomous operation features to operate the vehicle 108.

Similar to the controller 155, the controller 204 may include a program memory 208, one or more microcontrollers or microprocessors (MP) 210, a RAM 212, and an I/O circuit 216, all of which are interconnected via an address/data bus 214. The program memory 208 may include an operating system 226, a data storage 228, a plurality of software applications 230, and/or a plurality of software routines 240. The operating system 226, for example, may include one of a plurality of general purpose or mobile platforms, such as the Android™, iOS®, or Windows® systems, developed by Google Inc., Apple Inc., and Microsoft Corporation, respectively. Alternatively, the operating system 226 may be a custom operating system designed for autonomous vehicle operation using the on-board computer 114. The data storage 228 may include data such as user profiles and preferences, application data for the plurality of applications 230, routine data for the plurality of routines 240, and other data related to the autonomous operation features. In some embodiments, the controller 204 may also include, or otherwise be communicatively connected to, other data storage mechanisms (e.g., one or more hard disk drives, optical storage drives, solid state storage devices, etc.) that reside within the vehicle 108.

As discussed with reference to the controller 155, it should be appreciated that although FIG. 2 depicts only one microprocessor 210, the controller 204 may include multiple microprocessors 210. Similarly, the memory of the controller 204 may include multiple RAMs 212 and multiple program memories 208. Although FIG. 2 depicts the I/O circuit 216 as a single block, the I/O circuit 216 may include a number of different types of I/O circuits. The controller 204 may implement the RAMs 212 and the program memories 208 as semiconductor memories, magnetically readable memories, or optically readable memories, for example.

The one or more processors 210 may be adapted and configured to execute any of one or more of the plurality of software applications 230 or any one or more of the plurality of software routines 240 residing in the program memory 204, in addition to other software applications. One of the plurality of applications 230 may be an autonomous vehicle operation application 232 that may be implemented as a series of machine-readable instructions for performing the various tasks associated with implementing one or more of the autonomous operation features according to the autonomous vehicle operation method 300. Another of the plurality of applications 230 may be an autonomous communication application 234 that may be implemented as a series of machine-readable instructions for transmitting and receiving autonomous operation information to or from external sources via the communication unit 220. Still another application of the plurality of applications 230 may include an autonomous operation monitoring application 236 that may be implemented as a series of machine-readable instructions for sending information regarding autonomous operation of the vehicle to the server 140 via the network 130.

The plurality of software applications 230 may call various of the plurality of software routines 240 to perform functions relating to autonomous vehicle operation, monitoring, or communication. In some embodiments, the plurality of software routines may further assess risk levels or determine insurance policy costs and adjustments. One of the plurality of software routines 240 may be a configuration routine 242 to receive settings from the vehicle operator to configure the operating parameters of an autonomous operation feature. Another of the plurality of software routines 240 may be a sensor control routine 244 to transmit instructions to a sensor 120 and receive data from the sensor 120. Still another of the plurality of software routines 240 may be an autonomous control routine 246 that performs a type of autonomous control, such as collision avoidance, lane centering, and/or speed control. In some embodiments, the autonomous vehicle operation application 232 may cause a plurality of autonomous control routines 246 to determine control actions required for autonomous vehicle operation. Similarly, one of the plurality of software routines 240 may be a monitoring and reporting routine 248 that monitors and transmits information regarding autonomous vehicle operation to the server 140 via the network 130. Yet another of the plurality of software routines 240 may be an autonomous communication routine 250 for receiving and transmitting information between the vehicle 108 and external sources to improve the effectiveness of the autonomous operation features.

Any of the plurality of software routines 240 may be designed to operate independently of the software applications 230 or in conjunction with the software applications 230 to implement modules associated with the methods discussed herein using the microprocessor 210 of the controller 204. Additionally, or alternatively, the software applications 230 or software routines 240 may interact with various hardware modules that may be installed within or connected to the mobile device 110 or the on-board computer 114. Such modules may implement part of all of the various exemplary methods discussed herein or other related embodiments.

For instance, such modules may include a vehicle control module for determining and implementing control decisions to operate the vehicle 108, a system status module for determining the operating status of autonomous operation features, a monitoring module for monitoring the operation of the vehicle 108, a remediation module for correcting abnormal operating states of autonomous operation features, an insurance module for determining risks and costs associated with operation of the vehicle 108, an alert module for generating and presenting alerts regarding the vehicle 108 or the vehicle operator, a risk assessment module for determining risks associated with operation of the vehicle 108 by the autonomous operation features or by the vehicle operator, an identification module for identifying or verifying the identity of the vehicle operator, an information module for obtaining information regarding a vehicle operator or vehicle 108, a use cost module for determining costs associated with operation of the vehicle 108, a comparison module for comparing one or more costs associated with owning or operating the vehicle 108, an update module for updating an autonomous operation feature of the vehicle 108, and/or other modules.

When implementing the exemplary autonomous vehicle operation method 300, the controller 204 of the on-board computer 114 may implement a vehicle control module by the autonomous vehicle operation application 232 to communicate with the sensors 120 to receive information regarding the vehicle 108 and its environment and process that information for autonomous operation of the vehicle 108. In some embodiments, including external source communication via the communication component 122 or the communication unit 220, the controller 204 may further implement a communication module based upon the autonomous communication application 234 to receive information for external sources, such as other autonomous vehicles, smart infrastructure (e.g., electronically communicating roadways, traffic signals, or parking structures), or other sources of relevant information (e.g., weather, traffic, local amenities). Some external sources of information may be connected to the controller 204 via the network 130, such as the server 140 or internet-connected third-party databases (not shown). Although the autonomous vehicle operation application 232 and the autonomous communication application 234 are shown as two separate applications, it should be understood that the functions of the autonomous operation features may be combined or separated into any number of the software applications 230 or the software routines 240.

In some embodiments, the controller 204 may further implement a monitoring module by the autonomous operation monitoring application 236 to communicate with the server 140 to provide information regarding autonomous vehicle operation. This may include information regarding settings or configurations of autonomous operation features, data from the sensors 120 regarding the vehicle environment, data from the sensors 120 regarding the response of the vehicle 108 to its environment, communications sent or received using the communication component 122 or the communication unit 220, operating status of the autonomous vehicle operation application 232 and the autonomous communication application 234, and/or commands sent from the on-board computer 114 to the control components (not shown) to operate the vehicle 108. The information may be received and stored by the server 140 implementing the autonomous operation information monitoring application 141, and the server 140 may then determine the effectiveness of autonomous operation under various conditions by implementing the feature evaluation application 142 and the compatibility evaluation application 143. The effectiveness of autonomous operation features and the extent of their use may be further used to determine risk associated with operation of the autonomous vehicle by the server 140 implementing a risk assessment module or insurance module associated with the risk assessment application 144.

In addition to connections to the sensors 120, the mobile device 110 or the on-board computer 114 may include additional sensors, such as the GPS unit 206 or the accelerometer 224, which may provide information regarding the vehicle 108 for autonomous operation and other purposes. Furthermore, the communication unit 220 may communicate with other autonomous vehicles, infrastructure, or other external sources of information to transmit and receive information relating to autonomous vehicle operation. The communication unit 220 may communicate with the external sources via the network 130 or via any suitable wireless communication protocol network, such as wireless telephony (e.g., GSM, CDMA, LTE, etc.), Wi-Fi (802.11 standards), WiMAX, Bluetooth, infrared or radio frequency communication, etc. Furthermore, the communication unit 220 may provide input signals to the controller 204 via the I/O circuit 216. The communication unit 220 may also transmit sensor data, device status information, control signals, and/or other output from the controller 204 to one or more external sensors within the vehicle 108, mobile devices 110, on-hoard computers 114, and/or servers 140.

Figure 3:
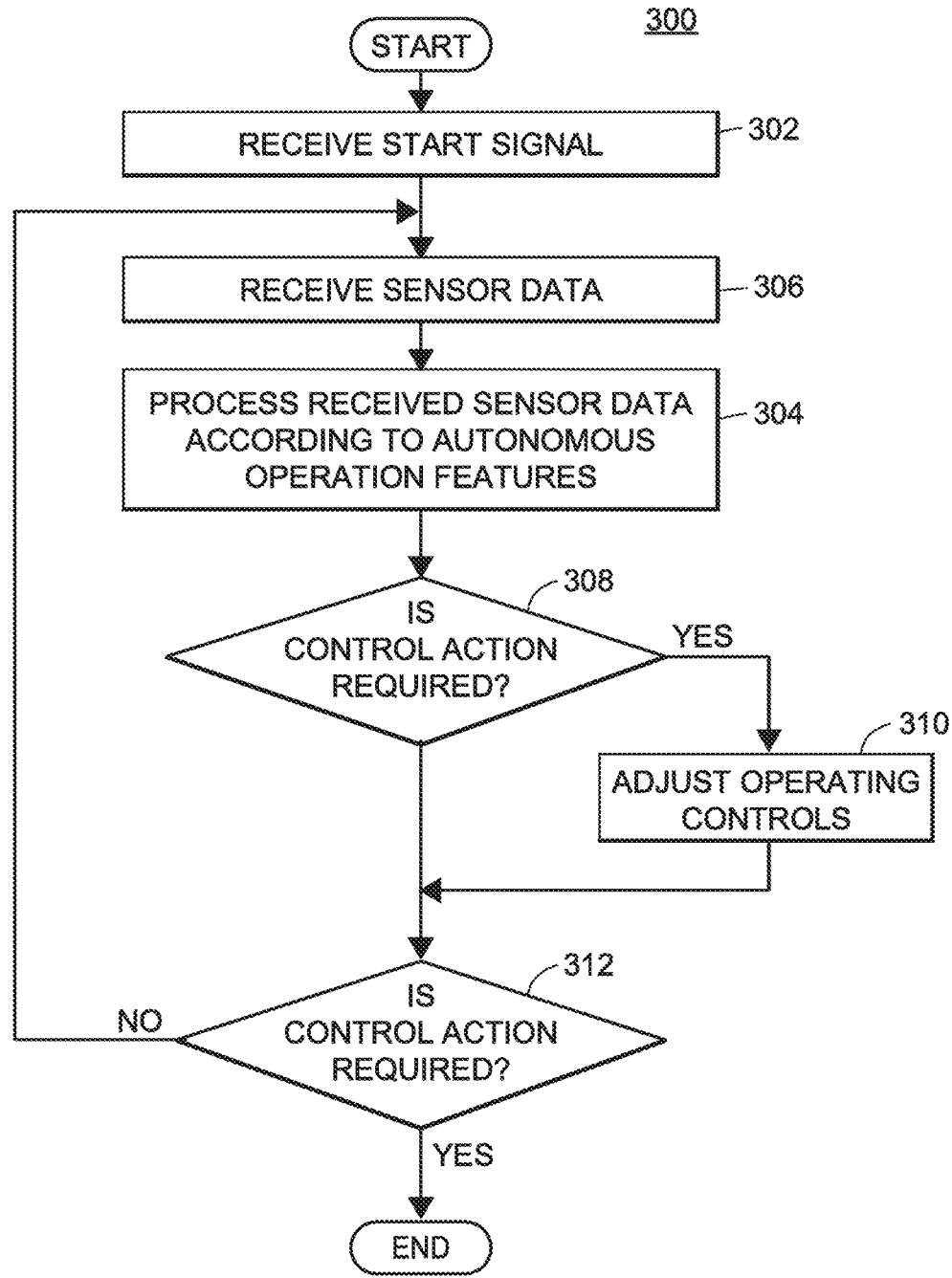
FIG. 3 illustrates a flow diagram of an exemplary autonomous vehicle operation method in accordance with the presently described embodiments.

The mobile device 110 and/or the on-board computer 114 may include a user-input device (not shown) for receiving instructions or information from the vehicle operator, such as settings relating to an autonomous operation feature. The user-input device (not shown) may include a "soft" keyboard that is displayed on the display 202, an external hardware keyboard communicating via a wired or a wireless connection (e.g., a Bluetooth keyboard), an external mouse, a microphone, or any other suitable user-input device. The user-input device (not shown) may also include a microphone capable of receiving user voice input.
Exemplary Autonomous Vehicle Operation Method FIG. 3 illustrates a flow diagram of an exemplary autonomous vehicle operation method 300, which may be implemented by the autonomous vehicle insurance system 100. The method 300 may begin at block 302 when the controller 204 receives a start signal. The start signal may be a command from the vehicle operator through the user-input device to enable or engage one or more autonomous operation features of the vehicle 108. In some embodiments, the vehicle operator 108 may further specify settings or configuration details for the autonomous operation features. For fully autonomous vehicles, the settings may relate to one or more destinations, route preferences, fuel efficiency preferences, speed preferences, and/or other configurable settings relating to the operation of the vehicle 108. In some embodiments, fully autonomous vehicles may include additional features or settings permitting them to operate without passengers or vehicle operators within the vehicle. For example, a fully autonomous vehicle may receive an instruction to find a parking space within the general vicinity, which the vehicle may do without the vehicle operator. The vehicle may then be returned to a selected location by a request from the vehicle operator via a mobile device 110 or otherwise. This feature may further be adapted to return a fully autonomous vehicle if lost or stolen.

For other autonomous vehicles, the settings may include enabling or disabling particular autonomous operation features, specifying thresholds for autonomous operation, specifying warnings or other information to be presented to the vehicle operator, specifying autonomous communication types to send or receive, specifying conditions under which to enable or disable autonomous operation features, and/or specifying other constraints on feature operation. For example, a vehicle operator may set the maximum speed for an adaptive cruise control feature with automatic lane centering. In some embodiments, the settings may further include a specification of whether the vehicle 108 should be operating as a fully or partially autonomous vehicle. In embodiments where only one autonomous operation feature is enabled, the start signal may consist of a request to perform a particular task (e.g., autonomous parking) and/or to enable a particular feature (e.g., autonomous braking for collision avoidance). In other embodiments, the start signal may be generated automatically by the controller 204 based upon predetermined settings (e.g., when the vehicle 108 exceeds a certain speed and/or is operating in low-light conditions). In some embodiments, the controller 204 may generate a start signal when communication from an external source is received (e.g., when the vehicle 108 is on a smart highway or near another autonomous vehicle).

After receiving the start signal at block 302, the controller 204 may receive sensor data from the sensors 120 during vehicle operation at block 304. In some embodiments, the controller 204 may also receive information from external sources through the communication component 122 and/or the communication unit 220. The sensor data may be stored in the RAM 212 for use by the autonomous vehicle operation application 232. In some embodiments, the sensor data may be recorded in the data storage 228 and/or transmitted to the server 140 via the network 130. The sensor data may alternately either be received by the controller 204 as raw data measurements from one of the sensors 120 and/or may be preprocessed by the sensor 120 prior to being received by the controller 204. For example, a tachometer reading may be received as raw data and/or may be preprocessed to indicate vehicle movement or position. As another example, a sensor 120 comprising a radar and/or LIDAR unit may include a processor to preprocess the measured signals and send data representing detected objects in 3-dimensional space to the controller 204.

The autonomous vehicle operation application 232, other applications 230, and/or routines 240 may cause the controller 204 to process the received sensor data at block 306 in accordance with the autonomous operation features. The controller 204 may process the sensor data to determine whether an autonomous control action is required and/or to determine adjustments to the controls of the vehicle 108. For example, the controller 204 may receive sensor data indicating a decreasing distance to a nearby object in the vehicle's path and process the received sensor data to determine whether to begin braking (and, if so, how abruptly to slow the vehicle 108). As another example, the controller 204 may process the sensor data to determine whether the vehicle 108 is remaining with its intended path (e.g., within lanes on a roadway). If the vehicle 108 is beginning to drift or slide (e.g., as on ice or water), the controller 204 may determine appropriate adjustments to the controls of the vehicle to maintain the desired bearing. If the vehicle 108 is moving within the desired path, the controller 204 may nonetheless determine whether adjustments are required to continue following the desired route (e.g., following a winding road). Under some conditions, the controller 204 may determine to maintain the controls based upon the sensor data (e.g., when holding a steady speed on a straight road).

When the controller 204 determines an autonomous control action is required at block 308, the controller 204 may cause the control components of the vehicle 108 to adjust the operating controls of the vehicle to achieve desired operation at block 310. For example, the controller 204 may send a signal to open or close the throttle of the vehicle 108 to achieve a desired speed. Alternatively, the controller 204 may control the steering of the vehicle 108 to adjust the direction of movement. In some embodiments, the vehicle 108 may transmit a message or indication of a change in velocity or position using the communication component 122 and/or the communication unit 220, which signal may be used by other autonomous vehicles to adjust their controls. As discussed further below, the controller 204 may also log or transmit the autonomous control actions to the server 140 via the network 130 for analysis.

The controller 204 may continue to receive and process sensor data at blocks 304 and 306 until an end signal is received by the controller 204 at block 312. The end signal may be automatically generated by the controller 204 upon the occurrence of certain criteria (e.g., the destination is reached or environmental conditions require manual operation of the vehicle 108 by the vehicle operator). Additionally, or alternatively, the vehicle operator may pause, terminate, and/or disable the autonomous operation feature or features using the user-input device or by manually operating the vehicle's controls, such as by depressing a pedal or turning a steering instrument. When the autonomous operation features are disabled or terminated, the controller 204 may either continue vehicle operation without the autonomous features or may shut off the vehicle 108, depending upon the circumstances.

Where control of the vehicle 108 must be returned to the vehicle operator, the controller 204 may ale1i the vehicle operator in advance of returning to manual operation. The alert may include a visual, audio, and/or other indication to obtain the attention of the vehicle operator. In some embodiments, the controller 204 may further determine whether the vehicle operator is capable of resuming manual operation before terminating autonomous operation. If the vehicle operator is determined not be capable of resuming operation, the controller 204 may cause the vehicle to stop and/or take other appropriate action.

Exemplary Monitoring Method During Operation

FIG. 4 illustrates a flow diagram depicting an exemplary monitoring method 400 during vehicle operation, which may be implemented by the autonomous vehicle insurance system 100. The method 400 may monitor the operation of the vehicle 108 and adjust risk levels and rates based upon vehicle use. Although the exemplary embodiment is described as primarily performed by the on-board computer 114, the method 400 may be implemented by the mobile device 110, the on-board computer 114, the server 140, or a combination thereof. Upon receiving an indication of vehicle operation at block 402, the on-board computer 114 may determine the configuration and operating status of the autonomous operation features (including the sensors 120 and the communication component 122) at block 404. The identity of the vehicle operator may be determined and/or verified at block 406, which identity may be used to determine or receive a vehicle operator profile at block 408. The vehicle operator profile may contain information regarding the vehicle operator's ability to manually operate the vehicle and/or past use of autonomous operation features by the vehicle operator. Information from the sensors 120 and/or external data from the communication component 122 may be used at block 410 to determine environmental conditions in which the vehicle 108 is operating. Together, this information determined at blocks 404-410 may be used at block 412 to determine one or more risk levels associated with operation of the vehicle, from which may be determined a costs associated with an insurance policy at block 414. In some embodiments, information regarding the determined cost may be presented to the vehicle operator or other insurance customer associated with the vehicle 108 at block 416. In still further embodiments, the vehicle operator and/or insurance customer may be presented with recommendations or options regarding the cost associated with the insurance policy at block 418. Presentation of options may assist the vehicle operator and/or insurance customer in reducing the cost by allowing the vehicle operator and/or insurance customer to select a lower-cost option (e.g., by adjusting the settings associated with the autonomous operation features). In some embodiments, the vehicle operator and/or insurance customer may be able to select one or more of the options to effect an adjustment in the risk levels and/or insurance cost.

The method 400 may continue monitoring operation of the vehicle 108 at block 420, and adjustments may be made to the risk levels and insurance costs. If the settings associated with the autonomous operation features are determined to have changed at block 422 (e.g., as a result of the vehicle operator taking manual operation of additional controls), the one or more risk levels may be determined based upon the new settings at block 412, in which case the blocks 414-422 may be repeated. When no changes have been made to the settings, the method 400 may further check for changes to the environmental conditions and/or operating status of the autonomous operation features at block 424. If changes are determined to have occurred at block 424, the one or more risk levels may be determined based upon the new settings at block 412, as at block 422. When no changes have occurred, the method 400 may determine whether vehicle operations are ongoing or whether operation is complete at block 426. When vehicle operation is ongoing, the method 400 may continue to monitor vehicle operation at block 420. When vehicle operation is complete, information regarding operation of the vehicle may be recorded at block 428, at which point the method 400 may terminate.

At block 402, the on-board computer 114 may receive an indication of vehicle operation. This indication may be received from the vehicle operator (either directly or through the mobile device 110), and/or it may be generated automatically. For example, the on-board computer 114 or the mobile device 110 may automatically generate an indication of vehicle operation when the vehicle starts operation (e.g., upon engine ignition, system power-up, movement of the vehicle 108, etc.). Upon receiving the indication of vehicle operation, the onboard computer 114 may initiate a system check and/or begin recording information regarding operation of the vehicle 108.

At block 404, the on-board computer 114 may determine the configuration and operating status of one or more autonomous operation features of the vehicle 108. This may include determining the configuration, settings, and/or operating status of one or more hardware or software modules for controlling part or all of the vehicle operation, aftermarket components disposed within the vehicle to provide information regarding vehicle operation, and/or sensors 120 disposed within the vehicle. In some embodiments, a software version, model version, and/or other identification of the feature or sensor may be determined. In further embodiments, the autonomous operation feature may be tested to assess proper functioning, which may be accomplished using a test routine or other means. Additionally, the sensors 120 or the communication component 122 may be assessed to determine their operating status (e.g., quality of communication connections, signal quality, noise, responsiveness, accuracy, etc.). In some embodiments, test signals may be sent to one or more of the sensors 120, responses to which may be received and/or assessed by the on-board computer to determine operating status. In further embodiments, signals received from a plurality of sensors may be compared to determine whether any of the sensors are malfunctioning. Additionally, signals received from the sensors may be used, in some embodiments, to calibrate the sensors.

At block 406, the on-board computer 114 may determine the identity of the vehicle operator. To determine the identity of the vehicle operator, the on-board computer 114 may receive and process information regarding the vehicle operator. In some embodiments, the received information may include sensor data from one or more sensors 120 configured to monitor the interior of the vehicle. For example, a camera or other photographic sensor may provide photographic information regarding the vehicle operator, which may be processed and compared with other photographic data for a plurality of persons to determine the identity of the vehicle operator. In further embodiments, the on-board computer may receive information from a mobile computing device associated with the vehicle operator, such as a mobile phone or wearable computing device. For example, a mobile phone may connect to the on-board computer 114, which may identify the vehicle operator. Additional steps may be taken to verify the identity of the vehicle operator, such as comparing a weight sensed on a seat or use of voice recognition algorithms.

At block 408, the on-board computer 114 may determine and/or access a vehicle operator profile based upon the identity of the vehicle operator determined at block 406. The vehicle operator profile may include information regarding the vehicle operator's style of operating the vehicle, including information regarding past operation of one or more vehicles by the vehicle operator. This information may further contain past vehicle operator selections of settings for one or more autonomous operation features. In some embodiments, the on-board computer 114 may request or access the vehicle operator profiled based upon the determined identity. In other embodiments, the on-board computer 114 may generate the vehicle operator profile from information associated with the identified vehicle operator. The vehicle operator profile may include information relating to one or more risks associated with operation of the vehicle by the vehicle operator. For example, the vehicle operator profile for a driver may include information relating to risk levels based upon past driving patters or habits in a variety of relevant environments, which may include risk levels associated with manual operation of the vehicle by the driver. In some embodiments, the vehicle operator profile may include information regarding default settings used by the vehicle operator for the autonomous operation features.

At block 410, the on-board computer 114 may determine environmental conditions within which the vehicle 108 is or is likely to be operating. Such environmental conditions may include weather, traffic, road conditions, time of day, location of operation, type of road, and/or other information relevant to operation of the vehicle. The environmental conditions may be determined based upon signals received from the sensors 120, from external data received through the communication component 122, and/or from a combination of sources. The environmental conditions may then be used in determining risk levels associated with operation of the vehicle 108.

At block 412, the on-board computer may determine one or more risk levels associated with operation of the vehicle 108. The risk levels may be determined based upon a combination of risk factors relating to the autonomous operation features and/or risk factors relating to the vehicle operation. Risks associated with the autonomous operation features may be determined based upon the configuration and/or operating status of the autonomous operation features, the settings of the autonomous operation features, and the vehicle environment. Risks associated with the vehicle operation may be determined based upon the autonomous operation features settings (i.e., the extent to which the vehicle operator will be controlling vehicle operations) and/or the vehicle operator profile. The combined risk may account for the likelihood of the autonomous operation features and/or the vehicle operator controlling vehicle operations with respect to relevant functions of the vehicle 108.

At block 414, the on-board computer 114 may determine a cost associated with an insurance policy based upon the one or more risks. In some embodiments, the server 140 may receive information regarding the vehicle operator and the autonomous operation features and/or may determine the cost associated with the insurance policy based upon the risks. The cost may be based upon risk levels associated with separate autonomous operation features, interaction between autonomous operation features, the design and capabilities of the vehicle 108, the past operating history of the vehicle operator as included in the vehicle operator profile, and/or other information regarding the probability of an accident, collision, and/or other loss event involving the vehicle 108. Each of the separate risks may depend upon the environmental conditions, and the risks may be weighted based upon the likelihood of each situation. In some embodiments, a total risk may be determined relating to operation of the vehicle under foreseeable conditions with specific settings and configurations of autonomous operation features by a specific vehicle operator. The total risk may be used to determine one or more costs associated with the insurance policy, such as a premium and/or discount.

In some embodiments, information regarding the cost associated with the insurance policy may be presented to the vehicle operator or insurance customer at block 416. The information may be presented by a display, such as the display 202 of the on-board computer 114 or the mobile device 110. The information may be presented either for informational purposes or to receive acceptance of the vehicle operator or insurance customer. The insurance cost information may include an indication of one or more of a premium, rate, rating, discount, reward, special offer, points level, program, refund, and/or other costs associated with one or more insurance policies. Additionally, or alternatively, summary information may be presented regarding insurance costs, including a risk level (e.g., high risk, low risk, a risk/cost level on a spectrum, etc.). In some embodiments, presentation of insurance cost information may be suppressed or delayed (e.g., cost information may be presented in summary form on a periodic billing statement).

In further embodiments, options or recommendations regarding the cost associated with the insurance policy may be presented to the vehicle operator or insurance customer at block 418. The options or recommendations may likewise be presented by a display, such as the display 202 of the on-board computer 114 and/or the mobile device 110. The options or recommendations may include information regarding costs associated with other settings or configurations of the autonomous operation features (e.g., enabling additional features, selecting an operating mode with lower risks under the determined environmental conditions, etc.). In some embodiments, the recommendations or options may be presented for informational purposes only, requiring the vehicle operator or insurance customer to make any adjustments separately (e.g., through a settings module or other means of adjusting settings for the autonomous operation features). In other embodiments, the vehicle operator or insurance customer may select one or more of the options, whereby adjustments to the configuration or settings of the autonomous operation features may be caused to be implemented by the on-board computer 114 or other controlling device. In some embodiments, the options or recommendations may include options or recommendations to update the software version of one or more autonomous operation features, in which case information regarding a cost associated with updating the features (if applicable) may be presented. Once the information and/or options or recommendations regarding insurance costs have been presented at blocks 416-418 (including, in some embodiments, while such presentation is occurring), the on-board computer 114 may monitor operation of the vehicle 108.

At block 420, the on-board computer 114 may monitor operation of the vehicle 108, including autonomous operation feature control decisions, signals from the sensors 120, external data from the communication component 122, and/or control decisions of the vehicle operator. Monitoring vehicle operation may include monitoring data received directly from the features, sensors, and/or other components, as well as summary information regarding the condition, movement, and/or environment of the vehicle 108. The on-board computer 114 and/or mobile device 110 may cause the operating data to be stored or recorded, either locally in the data storage 228 and/or via server 140 in the program memory 160 and/or the database 146. Monitoring may continue until vehicle operation is complete (e.g., the vehicle has reached its destination and shut down), including during any updates or adjustments.

At block 422, the on-board computer 114 may determine whether any changes have been made to the settings or configuration of the autonomous operation features. If such changes or adjustments have been made, the on-board computer 114 may proceed to determine new risk levels and insurance costs at blocks 412-414 and/or present the information to the vehicle operator or insurance customer at blocks 416-418, as discussed above. In some embodiments, minor changes below a minimum change threshold may be ignored when determining whether any changes have been made. In further embodiments, the cumulate effect of a plurality of such minor changes below the minimum change threshold may be considered as a change at block 422 when the cumulative effect of the minor changes reaches and/or exceeds the minimum change threshold. When no changes to the settings or configuration of the autonomous operation features are determined to have been made at block 422, the on-board computer 114 may further determine whether any changes in the environmental conditions and/or operating status of the autonomous operation features or sensors have occurred. Although these steps are illustrated separately for clarity, it should be understood that they may be further divided or combined in various embodiments.

At block 424, the on-hoard computer 114 may determine whether any changes have occurred to the environmental conditions of the vehicle 108 and/or the operating status of the autonomous operation features, sensors 120, or communication component 122. Such changes may occur when weather or traffic conditions change, when sensors 120 malfunction or become blocked by debris, and/or when the vehicle 108 leaves an area where external data is available via the communication component 122. When such changes occur, the risk levels associated with control of the vehicle 108 by the vehicle operator and the autonomous operation features may likewise change. Therefore, it may be advantageous to adjust the use of the autonomous operation features to account for such changes. Thus, the on-board computer 114 may proceed to determine new risk levels and insurance costs at blocks 412-414 and/or present the information to the vehicle operator or insurance customer at blocks 416-418, as discussed above, when such changes are determined to have occurred at block 424. Similar to the determination at block 422, minor changes below a minimum change threshold may be ignored at block 424, unless the cumulative effect of the changes reaches or exceeds the minimum change threshold. When no changes are determined to have occurred at block 424, the method 400 may continue to monitor the operation of the vehicle 108 until vehicle operation is determined to have ended.

At block 426, the on-board computer 114 may determine whether vehicle operations are complete. This may include determining whether a command to shut down the vehicle 108 has been received, whether the vehicle 108 has remained idle at a destination for a predetermined period of time, and/or whether the vehicle operator has exited the vehicle 108. Until operation is determined at block 426 to be complete (i.e., when the vehicle trip has concluded), the on-board computer 114 may continue to monitor vehicle operation at block 420, as discussed above. When operation is determined to be complete at block 426, the on-board computer 114 may further cause a record of the operation of the vehicle 108 to be made or stored. Such records may include operating data (in full or summary form) and may be used for assessing risks associated with one or more autonomous operation features or the vehicle operator. As noted above, in some embodiments, records of operating data may be generated and stored continually during operation. In some embodiments, the partial or completed records may be transmitted to the server 140 to be stored in the database 146. After completion and recordation of the vehicle operation, the method 400 may terminate.

Exemplary Methods for Determining Operating Status

FIG. 5 illustrates a flow diagram depicting an exemplary operating status assessment method 500 that may be used to determine operation status of the autonomous operation features, sensors 120, and/or communication component 122, as indicated in blocks 404 and 424 above. The method 500 may evaluate the autonomous operation features of the vehicle 108 (including sensors 120) and determine whether they are operating correctly, are malfunctioning, and/or are operating with impaired or degraded quality. Such determinations may be particularly important as the vehicle 108 ages or in environments that may block or damage sensors 120. In such cases, the original effectiveness of the autonomous operation features may be reduced as sensors become less accurate or processing of the sensor data is slowed (such as by software version updates that improve accuracy but require greater computational resources). The exemplary method 500 may be implemented regularly to ensure appropriate risk assessment, as well as periodically to certify the operating status level of the vehicle for roadworthiness or insurance rate adjustment. In some embodiments, periodic evaluation may be performed using special purpose computing devices and/or by licensed or authorized third parties. Periodic evaluation may further include more thorough testing and analysis of the vehicle 108, which may include testing at a test environment. Although the exemplary embodiment is described as primarily performed by the on-board computer 114, the method 500 may be implemented by the mobile device 110, the on-board computer 114, the server 140, or a combination thereof.

Upon receiving a request to determine the operating status of the autonomous operation features of the vehicle 108 at block 502, the configuration of the sensors 120 may be determined at block 504. The functioning of autonomous operation feature software routines may further be determined at block 506. A test signal may be transmitted to the sensors 120 at block 508, and/or sensor data may be received at block 510. The sensor data may include a response to the test signal, as well as other signals from the sensors based upon the vehicle environment or operation of the vehicle 108. Based upon the received information, the operating status of the autonomous operation features and components may be determined at block 512. If any impairments are detected at block 514, the method 500 may attempt to remediate the impairments at block 516. If impairments are detected to remain at block 518 after the remediation attempt, an alert may be generated and presented to the vehicle operator or an insurance customer at block 520. When no impairments are detected or after presentation of the alert, a report indicating the operational status of the autonomous operation features may be generated at block 522. In some embodiments, the report may be transmitted to an insurer at block 524, and/or a cost associated with an insurance policy associated with the vehicle 108 may be determined at block 526. The determined cost may be presented with the report at block 528 to the vehicle operator or insurance customer. Once the report has been presented, the exemplary method may end.

Figure 6:
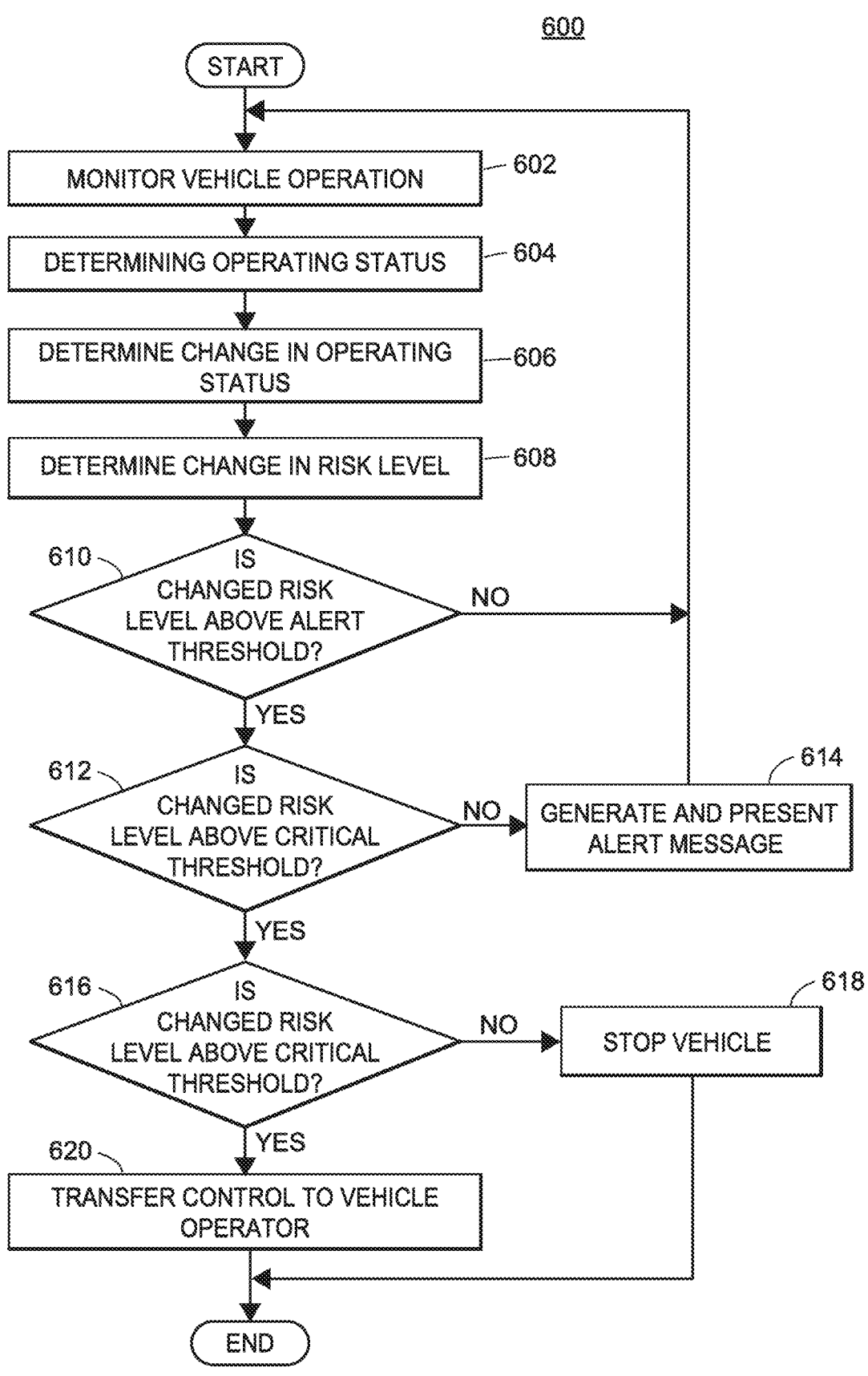
FIG. 6 illustrates a flow diagram of an exemplary operating status monitoring method in accordance with the presently described embodiments.

FIG. 6 illustrates a flow diagram of an exemplary operating status monitoring method 600 that may be used to determine operation status of the autonomous operation features, sensors 120, and/or communication component 122, in addition to or alternatively to the exemplary method 500 above. The method 600 may be implemented while the vehicle 108 is in operation to monitor the operating status of the autonomous operation features and components. The method 600 may monitor the vehicle operating data at block 602 to determine operating status of the autonomous operation features and components at block 604. When a change in operating status is detected at block 606, one or more corresponding changes in risk levels may be determined at block 608. If the changes in risk levels are determined to cause the risk levels to exceed an ale1i threshold but not a critical threshold at blocks 610 and 612, respectively, an ale1i is generated and presented to the vehicle operator at block 614. If the risk levels are determined to exceed the critical threshold at block 612, the method 600 may determine whether control of the vehicle 108 can be safely transferred to the vehicle operator at block 616. If the vehicle operator is prepared and able to assume control of the vehicle 108, then vehicle operation may be transferred to the vehicle operator at block 620. If control cannot be safely transferred, the vehicle 108 may cease operations and shut down at block 618. Once the vehicle 108 is no longer operating, the method 600 may terminate. Although the exemplary embodiment is described as primarily performed by the on-board computer 114, the method 600 may be implemented by the mobile device 110, the on-hoard computer 114, the server 140, or a combination thereof.

Exemplary Methods for Control Hand-Off

Figure 7A:
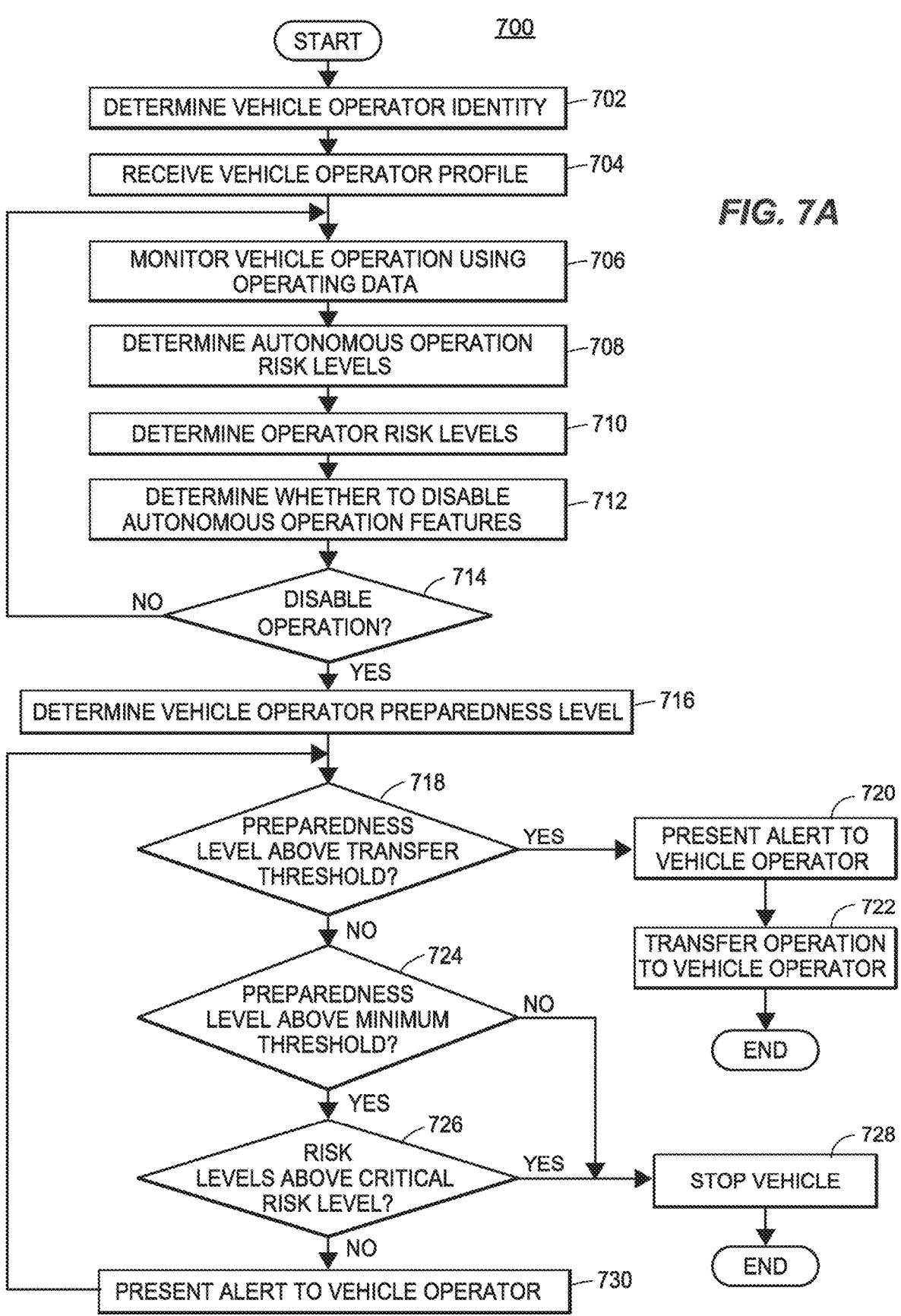
FIGS. 7A-B illustrate flow diagrams depicting exemplary vehicle operation handoff methods in accordance with the presently described embodiments.
Figure 7B:
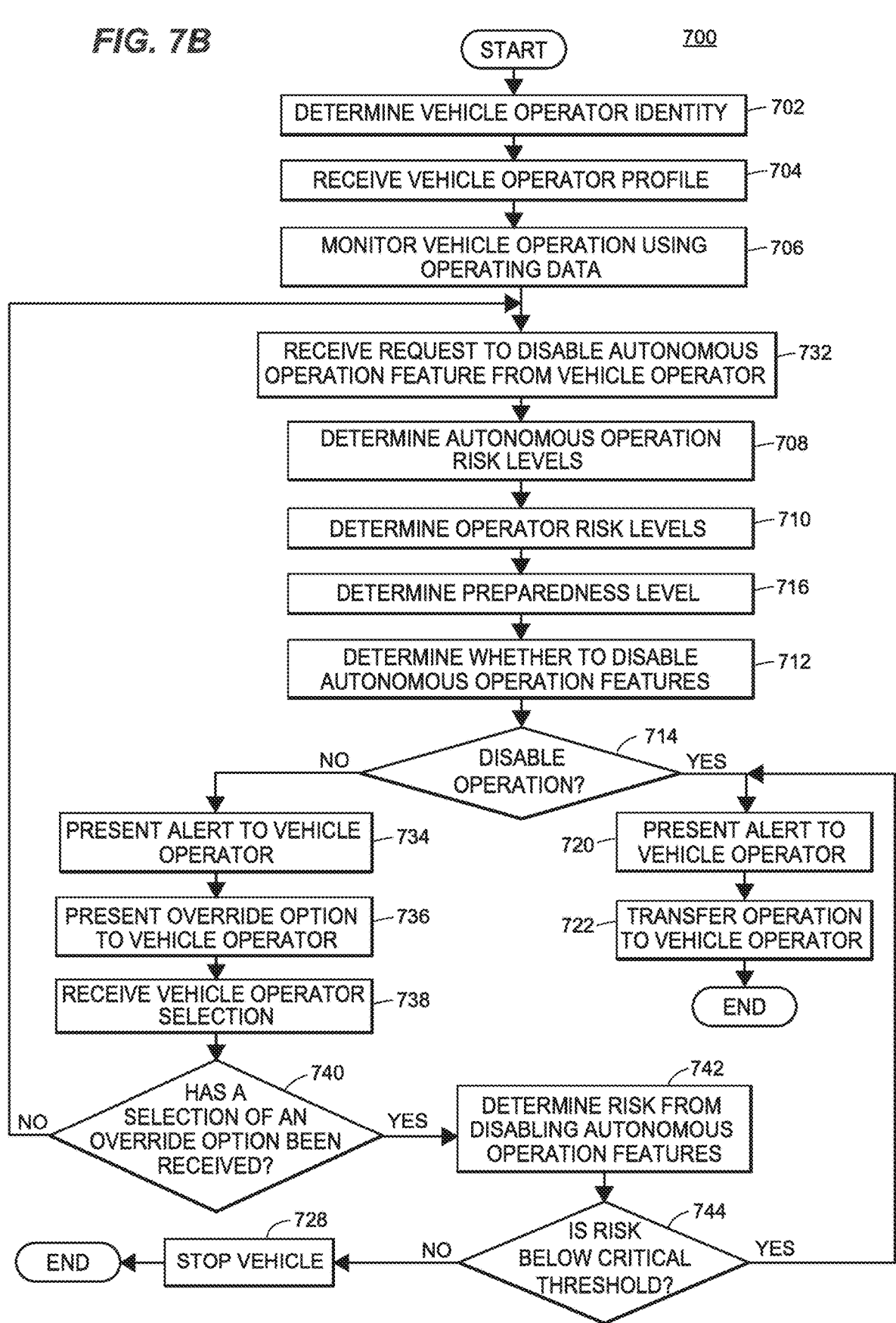

FIGS. 7A-B illustrate flow diagrams depicting exemplary vehicle operation handoff methods 700 that may be used to transfer operation of the vehicle 108 from one or more autonomous operation features to the vehicle operator. FIG. 7A illustrates hand-off of control when determined necessary based upon heightened risk levels associated with operation by the one or more autonomous operation features under the environmental conditions. FIG. 7B illustrates hand-off of control when requested by the vehicle operator while one or more autonomous operation features are performing vehicle control tasks. The methods 700 illustrated in FIGS. 7A and 7B may be combined or separately implemented in various embodiments. Although the exemplary embodiment is described as primarily performed by the on-board computer 114, the exemplary method 700 may be implemented by the mobile device 110, the on-board computer 114, the server 140, and/or a combination thereof.

Exemplary vehicle operation hand-off method 700 may be implemented at any time when one or more autonomous operation features are controlling part or all of the operation of the vehicle 108. The method 700 may begin by identifying the vehicle operator at block 702 and receiving a vehicle operator profile for the vehicle operator at block 704. At block 706, the operating data (including, in some embodiments, sensor data and external data) may be received and used to monitor operation of the vehicle 108. In some embodiments, a request to disable one or more autonomous operation features may be received from the vehicle operator at block 732. Autonomous risk levels associated with operation of the vehicle 108 by the autonomous operation features and operator risk levels associated with operation of the vehicle 108 by the vehicle operator may be determined at block 708 and 710, respectively. The determined risk levels may be used at block 712 to determine whether to disable one or more autonomous operation features. In some embodiments, the determination of whether to disable one or more autonomous operation features may further be based upon the preparedness level of the vehicle operator determined at block 716.

When it is determined to disable one or more autonomous operation features at block 714, the method 700 may transfer control to the vehicle operator. In some embodiments, this may include determining whether the vehicle operator is able to safely assume control by determining whether the vehicle operator's preparedness level is above a transfer threshold level at block 718. If so, an alert may be presented to the vehicle operator at block 720 to notify the vehicle operator of the transfer of control from the one or more autonomous operation features before transferring operation at block 722. If the vehicle operator's preparedness level is determined to be below the transfer threshold but above a minimum threshold at block 724, an alert may be presented at block 730 to attempt to prepare the vehicle operator to assume control if the risk levels associated with continued operation by the autonomous operation features do not exceed a critical risk threshold at block 726. Once the alert is presented to the vehicle operator at block 730, the vehicle operator's preparedness level may be determined again at block 716 and evaluated at block 718. If the risk levels exceed the critical threshold at block 726 or the vehicle operator's preparedness level is below the minimum threshold at block 724, the vehicle 108 may discontinue operation at block 728 and the method 700 may end.

When it is determined not to disable the one or more autonomous operation features at block 714, the method 700 may continue to monitor the operating data at block 706. If the vehicle operator requested that one or more autonomous operation features be disabled, the method 700 may present an alert at block 734 to notify the vehicle operator that disabling the autonomous operation features is not recommended. In some embodiments, options to override the determination not to disable the autonomous operation features may be presented to the vehicle operator at block 736, which the vehicle operator may select at block 738. If the vehicle operator is determined at block 740 to have not selected an option to override the determination, the method 700 may continue to monitor operation data at block 706. If the vehicle operator is determined at block 740 to have selected an option to override the determination, control of operation may be transferred from the one or more autonomous operation features to the vehicle operator. In some embodiments, one or more risk levels associated with disabling the autonomous operation features may be determined at block 742. If the risk levels are determined to be below a critical threshold at block 744, control may be transferred to the vehicle operator. If the risk levels meet or exceed the critical threshold at block 744, the vehicle 108 may instead discontinue operation at block 728 and the method 700 may end.

Exemplary Methods for Vehicle Operator Identification

Figure 8:
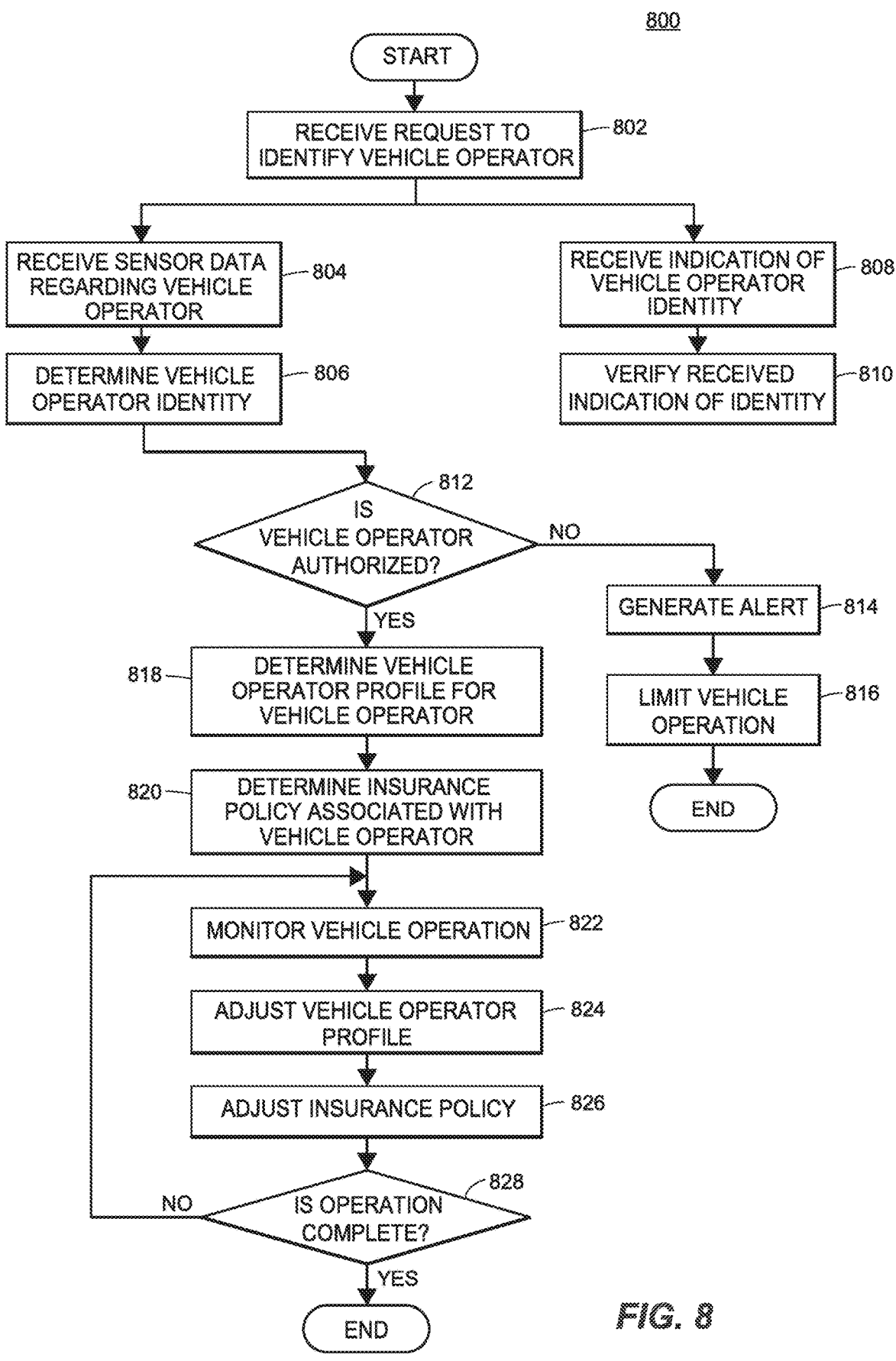
FIG. 8 illustrates a flow diagram depicting an exemplary vehicle operator identification method in accordance with the presently described embodiments.

FIG. 8 illustrates a flow diagram depicting an exemplary vehicle operator identification method 800 that may be used to adjust an insurance policy associated with the vehicle operator or vehicle 108. The exemplary method 800 may begin with receipt of a request to identify the vehicle operator of the vehicle at block 802. At blocks 804-810, the vehicle operator may be identified by sensor data or received indications of identity, such as from a mobile device 110. Once the identity of the vehicle operator has been determined (or cannot be determined), the method 800 may further determine whether the vehicle operator is authorized to operate the vehicle 108 at block 812. If the vehicle operator is not authorized, an ale1i may be generated and vehicle operations may be limited at blocks 814-816. If the vehicle operator is authorized, a vehicle operator profile associated with the vehicle operator may be obtained at block 818, and/or an insurance policy associated with the vehicle 108 or the vehicle operator may be identified at block 820. During vehicle operation, operating data of the vehicle 108 may be received and used to adjust the vehicle operator profile and the insurance policy at blocks 822-826. When vehicle operation has been determined to be complete at block 828, the method 800 may terminate. Although the exemplary embodiment is described as primarily performed by the on-board computer 114, the method 800 may be implemented by the mobile device 110, the on-board computer 114, the server 140, and/or a combination thereof.

Exemplary Methods for Monitoring Use by Vehicle Operators

Figure 9:
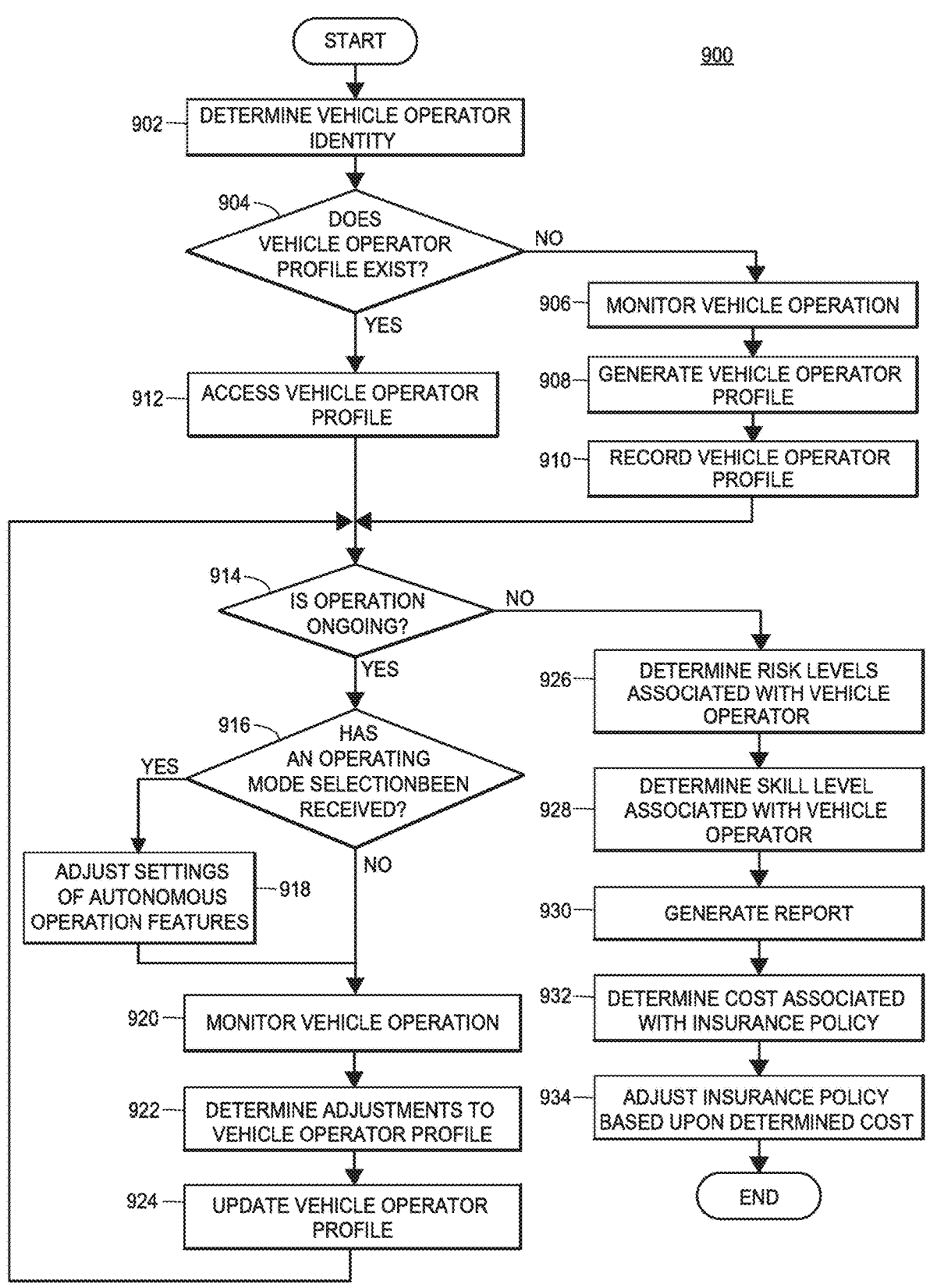
FIG. 9 illustrates a flow diagram depicting an exemplary vehicle operator use monitoring and evaluation method in accordance with the presently described embodiments.

FIG. 9 illustrates a flow diagram depicting an exemplary vehicle operator use monitoring and evaluation method 900 that may be used to determine skill or risk levels associated with a vehicle operator or adjust an insurance policy. The exemplary method 900 may begin with determining the identity of the vehicle operator at block 902. If a vehicle operator profile can be found for the vehicle operator at block 904, the vehicle operator profile may be accessed at block 912. If no vehicle operator profile can be found for the vehicle operator at block 904, a vehicle operator profile may be created based upon vehicle operations and stored for future use at blocks 906-910. The newly created vehicle operator profile may be generated at block 908 with vehicle operating data from only a short time period or may include only information regarding configuration and/or settings of the autonomous operation features, in which case operation of the vehicle may continue after the vehicle operator profile is generated. If operation is determined to be ongoing at block 914, vehicle operation may be monitored and the vehicle operator profile may be updated at blocks 916-924. In some embodiments, the vehicle operator may be able to select an option of a mode for vehicle operation. If such a mode selection is detected at block 916, the settings of the autonomous operation features may be adjusted at block 918. Vehicle operation may be monitored at block 920 based upon received operating data, which may be used to determine adjustments to the vehicle operator profile at block 922. The adjustments may then be used to update the vehicle operator profile at block 924. When operation is complete, the method 900 may determine risk or skill levels associated with the vehicle operator at blocks 926-928. These determined levels may be used at blocks 930-934 to generate a report or adjust an insurance policy. Although the exemplary embodiment is described as primarily performed by the on-board computer 114, the method 900 may be implemented by the mobile device 110, the on-hoard computer 114, the server 140, and/or a combination thereof.

The vehicle operator profile may include information regarding the vehicle operator, including an operating style of the vehicle operation. The operating style may include information regarding frequency with which the vehicle operator operates the vehicle manually, uses one or more autonomous operation features, selects one or more settings for the autonomous operation features, and/or takes control from the autonomous operation features under various conditions. The operating style may further include information regarding observed control decisions made by the vehicle operator, such as rate of acceleration, frequency of lane changes, use of vehicle signaling devices, distances maintained from other vehicles or pedestrians, and/or other aspects of vehicle operation. For example, vehicle operator decisions regarding how long to stop at a stop sign or when to begin accelerating from such a stop in the presence of other vehicles or pedestrians may be included in the operating style. The vehicle operator profile may further include information regarding vehicle operator skill levels, as described below. In some embodiments, the vehicle operator profile may include a risk profile or information regarding one or more risk levels associated with operation of the vehicle by the vehicle operator. Such risk levels may be associated with particular configurations or settings of autonomous operation features and/or particular conditions of the vehicle environment (e.g., time of day, traffic levels, weather, etc.).

In further embodiments, the vehicle operator profile may include information regarding attentiveness of the vehicle operator while the vehicle is being autonomously operated. For example, some vehicle operators may typically pay attention to road conditions while a vehicle is operating in a fully autonomous mode, while other vehicle operators may typically engage in other activities. In some embodiments, the vehicle operator profile may include information regarding decisions made by the vehicle operator regarding actions that would result in adjustments to costs associated with an insurance policy (e.g., accepting or rejecting recommendations to optimize autonomous operation feature use to lower insurance costs).

The vehicle operator profile or vehicle operator behavior data may indicate how well the specific vehicle operator drives in rain, snow, sleet, ice, heavy traffic, road construction, stop-and-go traffic, bumper-to-bumper traffic, country or rural traffic, and/or city or downtown street traffic. The current environment (or condition) may include or be rain, ice, snow, fog, heavy traffic, bumper-to-bumper traffic, road construction, city traffic, country or rural traffic, and/or may be associated with a type of road, such as a two-lane or four-lane highway, and/or downtown city street or other street having several traffic lights.

The operating mode may include one or more settings or configurations of autonomous operation features. For example, operating modes may include adjustments to settings that cause the autonomous operation features to control the vehicle 108 in a more or less aggressive manner with respect to speed, distance from other vehicles, distance from pedestrians, etc. As an example, the settings may cause the vehicle 108 to remain at least a minimum distance from other vehicles (which may depend upon vehicle speed or road conditions), and/or modes may set different minimum distances. Examples of modes may include a city driving mode, a highway driving mode, a rush operation mode, a smooth operation mode, a cautious mode, and/or a user-defined mode.

In some embodiments, an operating mode may be based upon the vehicle operator profile. For example, the vehicle profile may include information indicating an operating style of the vehicle operator based upon observations of control commands by the vehicle operator, which profile information may be used to generate an operation mode that mimics the style of the vehicle operator. Thus, if the vehicle operator typically stops at stop signs for a particular length of time, the operating style may mimic this length of time to provide an experience that seems normal or customary to the vehicle operator.

Exemplary Methods for Comparing Costs

FIG. 10 illustrates a flow diagram depicting an exemplary cost comparison method 1000 that may be used to compare costs associated with vehicles, some of which may include autonomous operation features. The exemplary method 1000 may begin by receiving a command to generate a comparison report between two or more alternative transportation options for an insurance customer or other user. The method 1000 may further receive information regarding one or more vehicle operators may be received at block 1004 and/or information regarding a first vehicle and a second vehicle at block 1006. The first and second vehicles may differ in autonomous operation features or other characteristics. Cost levels associated with obtaining, operating, and insuring the first vehicle and the second vehicle may be determined at block 1008, and/or a recommendation based upon the costs may be determined at block 1010. A report including the costs levels, recommendation, and/or related information may be generated at block 1012 and presented to the insurance customer or other user at block 1014. Additionally, one or more options may be presented along with the report at block 1016, such as options to perform another comparison or present additional information. If an option is selected at block 1018, the corresponding action may be performed at block 1020. Although the exemplary embodiment is described as primarily performed by the server 140, the method 1000 may be implemented by the mobile device 110, the on-board computer 114, the server 140, and/or a combination thereof.

Exemplary Methods for Updating Autonomous Operation Features

FIG. 11 illustrates a flow diagram depicting an exemplary autonomous operation feature update method 1100 that may be used to identify, recommend, and/or install updates to autonomous operation features in appropriate autonomous or semi-autonomous vehicles. In some embodiments, the updates may include software version updates. The exemplary method 1100 may begin with the receipt of an indication of an available update to an autonomous operation feature at block 1102, which may include an update to a version of autonomous operation feature software. A plurality of vehicles having the autonomous operation feature may be identified at block 1104 based upon recorded features or communication with the plurality of vehicles. A change in one or more risk levels associated with the update may be determined for some or all of the identified vehicles at block 1106, and/or a change in a cost associated with one or more of the plurality of vehicles may be determined at block 1108. If the determined changes in risk levels or insurance costs meet certain criteria for installing the update at block 1110, a notification regarding the update may be presented to an insurance customer at block 1112. The notification may further include information regarding costs associated with the update. If an indication of acceptance of the update is received at block 1114, the update may be installed at block 1116. Although the exemplary embodiment is described as primarily performed by the server 140, the method 1100 may be implemented by the mobile device 110, the on-board computer 114, the server 140, and/or a combination thereof.

Exemplary Methods for Repair of an Autonomous Vehicle

FIG. 12 illustrates a flow diagram depicting an exemplary autonomous vehicle repair method 1200 that may be used to determine repairs needed as a result of damage to an autonomous or semi-autonomous vehicle. The exemplary method 1200 may begin by receiving an indication of damage to the vehicle 108 at block 1202 and/or receiving operating data associated with the vehicle 108 at block 1204. Based upon the operating data, the type and extent of damage to the vehicle 108 may be determined at block 1206, and/or repairs needed to fix the damage may be determined at block 1208. Additionally, one or more expected costs (or ranges of costs) for the repairs may be estimated at block 1210. An insurance policy associated with the vehicle 108 may be identified, and/or a maximum payment for the repairs may be determined at block 1212 based upon the estimated costs and the insurance policy. Information regarding the estimated cost or costs and the maximum payment under the insurance policy may be presented to an insurance customer at block 1214. Additionally, options associated with the repairs may be presented to the insurance customer at block 1216, and/or a selection of one or more options may be received at block 1218. An insurer or other party may cause a payment to be made at block 1220 to the insurance customer, beneficiary, or other relevant party based upon the estimated costs of repairing the damage and the selected option. Although the exemplary embodiment is described as primarily performed by the server 140, the method 1200 may be implemented by the mobile device 110, the on-board computer 114, the server 140, and/or a combination thereof.

At block 1202, the on-board computer 114 or server 140 may receive an indication of damage to the vehicle 108. The indication may be received from a vehicle operator and/or insurance customer, and/or the indication may be automatically generated upon a determination of damage. For example, the sensors 120 may provide sensor data to the on-board computer 114 that indicates a collision with another vehicle or other object. Alternatively, the substantially simultaneous disconnection and/or malfunction of a plurality of sensors 120 located in close proximity within the vehicle 108 may cause the on-board computer 114 to generate an indication of damage to the vehicle 108.

At block 1204, the on-board computer 114 and/or server 140 may receive operating data regarding operation of the vehicle. The operating data may cover operation of the vehicle both before and after the damage occurred, covering a period of time without the damage and a period of time with the damage. The operating data may include information received from the sensors 120 and/or the communication component 122. The operating data may further include information regarding autonomous operation features, such as configurations or settings, and/or information regarding command controls issued by the autonomous operation features and/or vehicle operator. The operating data may further include information derived or determined from the sensor or other data, such as vehicle speed and/or direction. Where the vehicle is inoperable following the damage, the operating data for the time period with damage may include sensor data and/or other data regarding the vehicle and/or the vehicle environment. Such data may be useful in determining the likely extent of the damage by determining damaged areas and/or systems of the vehicle 108.

At block 1206, the server 140 may determine damage to the vehicle 108 based upon the received operating data. In some embodiments, the operating data may be compared against operating data for a plurality of previous instances of known vehicle damage stored within the database 146 to determine likely damage. Such assessment may be based information from similar vehicles (e.g., vehicles of the same make and model, body type, size, or production year). In some embodiments, the operating data may be processed to generate a model of the vehicle in its environment at the time of the damage. For example, the operating data may indicate relative speeds and/or trajectories of vehicles involved in a collision with the vehicle 108. This model may then be further used to determine likely damage based upon information regarding the vehicle 108 and/or previous loss reports for other vehicles. In some embodiments, the determined damage may be reviewed by a verification routine of the server 140 and/or by a reviewer to verify that the determined level of damage appears to match the actual level of damage. Verification may include assessing the operating status of the sensors 120 and/or communication component 122. In some embodiments, the damage may be determined based upon input from a special-purpose computing device or a human assessor.

At block 1208, the server 140 may determine one or more repairs associated with the determined damage to the vehicle 108. In some embodiments, the repairs may be determined based upon comparisons of information regarding previously repaired vehicles' damage and repairs. In further embodiments, the repairs may be determined based upon models and/or relationships between types of damage and types of repairs. The repairs may include replacing and/or fixing damage to one or more vehicle components, including the vehicle frame and body. In some embodiments, the repairs may include alternative likely repairs, such that performance of one repair may foreclose the necessity of another repair. For example, the operating data may indicate two or more probably types of damage, but only one type of damage may be present. Thus, repair of one type of likely damage would obviate the need to repair the other types of likely damage. In some embodiments, the repairs may include one or more general repair services and/or one or more specialty repair services. General repair services may be performed by most vehicle repair facilities, whereas specialty repair services may require specialized equipment, materials, and/or expertise to perform the repairs.

At block 1210, the server 140 may determine expected costs associated with the one or more repairs determined at block 1208. The costs may include both direct costs of repair, as well as indirect costs, such as vehicle rental while the vehicle 108 is being repaired. The costs may be determined based upon information regarding actual costs of repairs performed on a plurality of other vehicles. In some embodiments, the repair costs for other vehicles may be used to determine a range of expected costs and/or an average cost for each repair. The range of expected costs may further be used to determine one or more expected cost levels associated with the repairs, such as a median cost, a mean cost, a high cost or low cost (e.g., levels based upon percentages such as the 80th percentile or the 20th percentile of costs), costs associated with different likely damage levels, and/or indirect costs based upon the extent of the repairs. The costs may also be based upon comparisons of costs in one or more relevant geographic areas. For example, minor damage occurring during a long-distance trip may not preclude operation of the vehicle 108 through the remainder of the trip, in which case costs associated with repair in multiple geographic areas may be determined (e.g., an area where the damage occurred, an area corresponding to a destination of the trip, or an area corresponding to the home location of the vehicle operator or insurance customer). In some embodiments, the costs may be determined based upon quotes received from one or more repair facilities based upon the determined repairs and/or operating data.

At block 1212, the server 140 may determine one or more maximum payments for the repairs to the vehicle 108. The maximum payments may be based upon the determined costs of the repairs. In some embodiments, the maximum payment may be based upon the range of repair costs. For example, the maximum payment may be set to a level based upon the distribution of repair costs within the range, such that the maximum payment is equal to an actual cost of repairs for a vehicle at a certain percentile of vehicles within the actual repair cost range (e.g., 70th percentile). In further embodiments, the maximum payment may be based in whole or part upon the insurance policy under which payment may be made. For example, a maximum payment amount may be set by the insurance policy, which may, in some embodiments, be further limited based upon the expected costs and/or range of expected costs determined at block 1210.

At block 1214, the server 140 may cause the one or more expected costs to be presented to the insurance customer, using the display 202 and/or other means. In some embodiments, the maximum payment may be presented to the insurance customer together with the expected costs. For example, where a plurality of alternatives are presented regarding the repairs, each expected cost may include an indication of whether it is below the maximum payment.

At block 1216, the server 140 may cause one or more options regarding the repairs to be presented to the insurance customer. The options may indicate timing, extent, and/or location of the repairs and may be associated with different costs for the repairs. In some embodiments, the options may include options of one or more repair facilities at which the vehicle 108 may be repaired. Each facility may further be associated with a cost estimate and/or an estimate of a length of time required to complete the repairs. In some embodiments, the estimates of costs and/or time for each facility may be based upon the operating data and/or determined damage. In further embodiments, the estimates of costs and/or time for one or more of the repair facilities may be based upon quoted estimates solicited from the repair facilities received by the server 140. The options may be presented together with an indication of whether each exceeds the maximum payment, such as by a warning presented in connection with any options that exceed the maximum payment.

At block 1218, the server 140 may receive a selection of one or more of the options from the insurance customer or other authorized user. Upon receiving the selection, the server 140 may cause a payment to be made at block 1220 based upon the one or more selections. The payment may be made to the insurance customer and/or beneficiary of the insurance policy, or the payment may be made to a repair facility and/or other party associated with the repairs. In some embodiments, the server 140 may further facility the repairs by scheduling the repairs at a repair facility, arranging towing of the vehicle to the repair facility, and/or arranging a temporary replacement vehicle for the vehicle operator and/or insurance customer. Once all actions relating to the repair and/or payment have been implemented, the method 1200 may terminate.

Exemplary Methods for Infrastructure Communications

Figure 13:
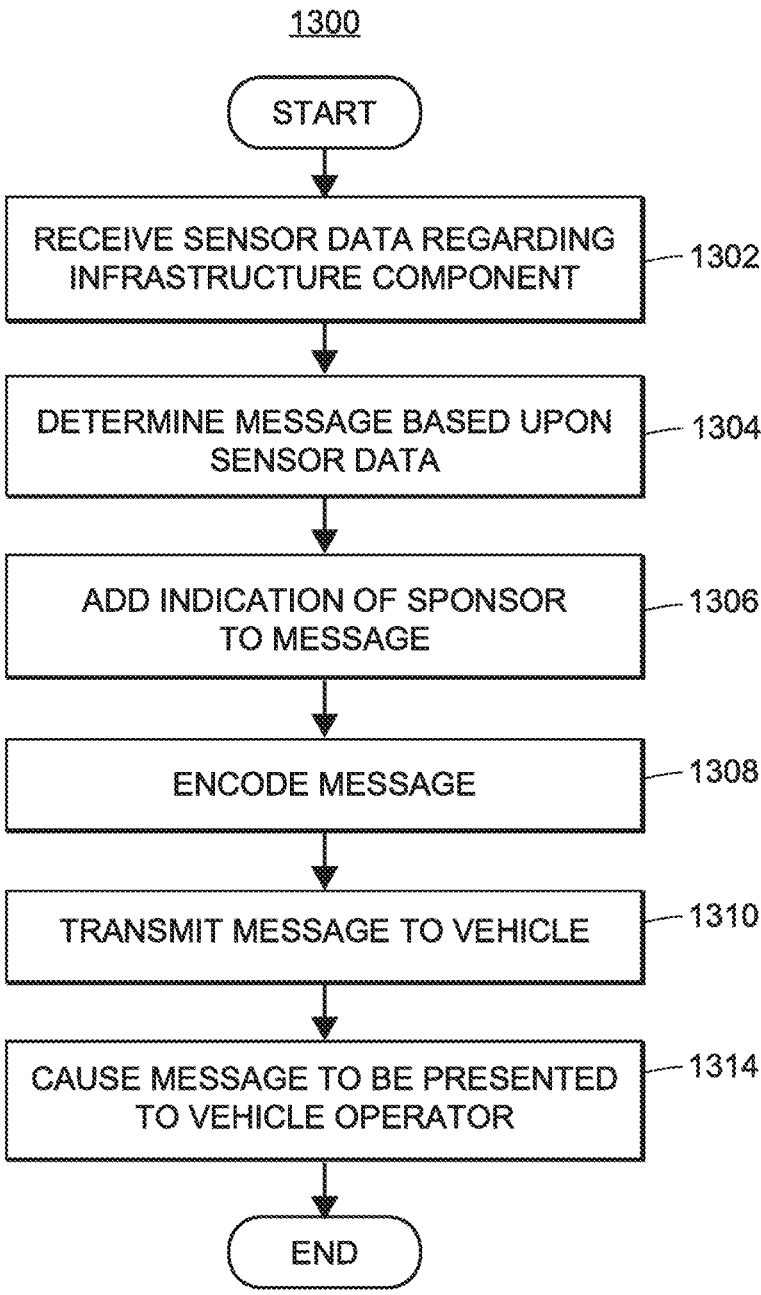
FIG. 13 illustrates a flow diagram depicting an exemplary infrastructure communication method in accordance with the presently described embodiments.

FIG. 13 illustrates a flow diagram depicting an exemplary infrastructure communication method 1300 that may be used to detect and communicate information regarding infrastructure components to vehicles. The exemplary method 1300 may begin with the infrastructure communication device 124 receiving information regarding the infrastructure component 126 from one or more sensors at block 1302. The information may be used at block 1304 to determine a message regarding the infrastructure component 126. In some embodiments, the message may be augmented at block 1306 by information associated with a sponsor or other party affiliated with the infrastructure communication device 124. The message may then be encoded at block 1308 and transmitted at block 1310, which may cause the message to be presented to the vehicle operator of the vehicle 108 at block 1312. Although the exemplary embodiment describes one infrastructure communication device 124 communicating with one vehicle 108, it should be understood than any number of infrastructure communication devices 124 may communicate with any number of vehicles 108.

Accident Reconstruction

In one aspect, a computer-implemented method of accident reconstruction or fault determination may be provided. The method may include (1) gathering or collecting data from one or more vehicle-mounted sensors and/or one or more autonomous or semi-autonomous functionality or technology systems of a vehicle, via one or more processors (such as a smart vehicle controller and/or insurance provider remote processor or server) in wired or wireless communication with the one or more vehicle-mounted sensors and/or the one or more autonomous or semi-autonomous functionality or technology systems, the data showing operation of the vehicle and/or how the one or more autonomous or semi-autonomous functionality or technology systems performed before, during, and/or after a vehicle accident involving the vehicle, the vehicle being insured by an insurance provider; (2) reconstructing the scene of the vehicle accident and/or a series of events leading up to the vehicle accident, via the one or more processors; (3) determining, via the one or more processors, one or more causes of the vehicle accident (whether human driver error or faulty autonomous or semi-autonomous functionality or technology) based upon the reconstruction of the vehicle accident; (4) generating, updating, or adjusting, via the one or more processors, (i) an insurance claim associated with the vehicle accident, and/or (ii) an insurance policy, premium, rate, discount, or reward based upon the one or more causes of the vehicle accident determined from the reconstruction of the vehicle accident; and/or (5) communicating or transmitting, from the one or more processors, the insurance claim or insurance policy generated, updated, or adjusted to a mobile device of an insured or owner of the vehicle insured by the insurance provider. The method may include additional, fewer, or alternate actions, including those discussed elsewhere herein.

Emergency Services

In one aspect, a computer-implemented method of directing a route of an autonomous or semi-autonomous vehicle may be provided. The method may include (1) detecting, via a biometric device, that a driver or passenger of an autonomous or semi-autonomous vehicle is having a medical emergency, the autonomous or semi-autonomous vehicle being equipped with an autonomous or semi-autonomous vehicle functionality or technology; (2) sending or transmitting, from the biometric device, to one or more processors (such as vehicle-mounted processors, a smart vehicle controller, and/or an insurance provider remote processor or server), an indication that the driver or passenger is having the medical emergency; (3) in response to receiving the indication that the driver or passenger is having the medical emergency, (a) retrieving or receiving a GPS (Global Positioning System) position, at the one or more processors, from a vehicle-mounted GPS unit or a mobile device GPS unit, and/or (b) determining, via the one or more processors, a route from a current location of the autonomous or semi-autonomous vehicle to a hospital (or emergency room or other medical facility); (4) directing, via the one or more processors, one or more autonomous or semi-autonomous vehicle functionalities or technologies to drive the autonomous or semi-autonomous vehicle from the current location to the hospital; and/or (5) directing or controlling, via the one or more processors, a transmission or communication to the hospital, such as via wireless communication from a remote transmitter associated with an insurance provider and/or a vehicle-mounted transmitter, to indicate the current location of the autonomous or semiautonomous vehicle, the medical emergency of the driver or passenger, and/or the estimated arrival time of the autonomous or semi-autonomous vehicle at the hospital to facilitate medical response to the medical emergency. The method may include additional, fewer, or alternate actions, including those discussed elsewhere herein.

The medical emergency detected by the biometric device may be a heart attack, stroke, and/or seizure. The method may further include directing or controlling, via the one or more processors, a transmission from the autonomous or semi-autonomous vehicle to a police department and/or fire department indicating the medical emergency and/or requesting assistance to the current, an approximate, and/or expected (based upon current route) location of the autonomous or semi-autonomous vehicle.

The method may further include directing or controlling, via the one or more processors, a transmission from the autonomous or semi-autonomous vehicle to a mobile device of a family member of the driver or passenger indicating the medical emergency, current location, current route, and/or current destination of the autonomous or semi-autonomous vehicle.

Directing an Emergency Route

In one aspect, a computer-implemented method of directing an emergency route of an autonomous or semi-autonomous vehicle may be provided. The method may include (a) detecting, via a biometric device, that a driver or passenger of an autonomous or semiautonomous vehicle is having a medical emergency, the autonomous or semi-autonomous vehicle being equipped with an autonomous or semi-autonomous vehicle functionality or technology; (b) sending or transmitting, from the biometric device, to one or more processors (such as vehicle-mounted processors, a smart vehicle controller, and/or an insurance provider remote processor or server), an indication that the driver or passenger is having the medical emergency; (c) in response to receiving the indication that the driver or passenger is having the medical emergency, via the one or more processors: (1) directing one or more autonomous or semi-autonomous vehicle functionalities or technologies to automatically engage (such that the autonomous or semi-autonomous vehicle is self-driving without human interaction); (2) retrieving or receiving a current GPS (Global Position System) position of the autonomous or semi-autonomous vehicle (such as from a vehicle-mounted GPS unit or a GPS unit of a mobile device or wearable device associated with the driver or passenger); (3) determining a route from a current GPS location of the autonomous or semi-autonomous vehicle to a hospital (or emergency room or other medical facility); and/or (4) directing one or more autonomous or semi-autonomous vehicle functionalities or technologies to drive the autonomous or semiautonomous vehicle from the current GPS location to the hospital to facilitate the driver or passenger receiving medical assistance in a prompt and safe manner. The method may include additional, fewer, or alternate actions, including those discussed elsewhere herein.

For instance, the method may include directing or controlling, via the one or more processors, a transmission (such from a remote transmitter and/or from the autonomous or semiautonomous vehicle itself) to the hospital, such as via wireless communication from a remote transmitter and/or a vehicle-mounted transmitter, to indicate the current location of the autonomous or semi-autonomous vehicle, the medical emergency of the driver or passenger, and/or the estimated arrival time of the autonomous or semi-autonomous vehicle at the hospital to facilitate medical response to the medical emergency. The medical emergency detected by the biometric device may be a heart attack, stroke, and/or seizure.

The method may include directing or controlling, via the one or more processors, a transmission from the autonomous or semi-autonomous vehicle to a police department and/or fire department indicating the medical emergency and/or requesting assistance to the current, an approximate, and/or expected (based upon current route) location of the autonomous or semiautonomous vehicle. The method may include directing or controlling, via the one or more processors, a transmission from the autonomous or semi-autonomous vehicle to a mobile device of a family member of the driver or passenger indicating the medical emergency, current location, current route, and/or current destination of the autonomous or semi-autonomous vehicle.

According to certain aspects, with the customer's permission, it may be detected by sensors (such as vehicle-mounted sensors or mobile device sensors) that an occupant of the autonomous or semi-autonomous vehicle is experiencing a medical emergency. A nearby medical facility may be determined based upon the vehicle location and the detected medical emergency, such as via navigation unit or application running on the vehicle controller or mobile device. A route from the current vehicle location to the medical facility may be determined (such ashy the vehicle controller or mobile device), and the autonomous or semi-autonomous vehicle may be automatically directed or routed to the medical facility. A message may also be generated by the vehicle controller or mobile device, and transmitted to the medical facility to alert them that a person in need of timely medical assistance is on the way and/or their current location. Life and auto insurance discounts may be generated for risk averse customers based upon their vehicles having the emergency response functionality.

Also with the foregoing, a customer may opt into a rewards or other type of program, and willingly share their vehicle data with an insurance provider. In return, risk averse drivers and vehicle owners may receive discounts or insurance cost savings related to auto, life, and other types of insurance from the insurance provider.

Updating Insurance Policies

In one aspect, a computer-implemented method of updating an insurance policy may be provided. The method may include (a) gathering or receiving, at or via one or more processors (such as either a local processor associated with a smart vehicle and/or a remote processor or server associated with an insurance provider), data indicative of (1) vehicle usage, and/or (2) vehicle drivers for an insured vehicle; (b) analyzing the data, via the one or more processors, to determine (i) an amount and/or (ii) type of vehicle usage for each vehicle driver; (c) based upon the amount of vehicle usage for each vehicle driver and/or the type of vehicle usage for each vehicle driver, via the one or more processors, updating or adjusting an insurance policy (such as a premium, rate, rewards or points program, discount, etc.) for the insured vehicle; (d) transmitting, under the direction or control of the one or more processors, the updated or adjusted insurance policy (or otherwise causing the updated or adjusted insurance policy to be presented or displayed to the insured) to a mobile device of the insured for their review, modification, and/or approval; and/or (e) receiving, at or via the one or more processors, from the mobile device of the insured (such as via wireless communication) an approval of the updated or adjusted insurance policy of the insured to facilitate more accurate insurance pricing and/or insurance cost savings. The method may include additional, fewer, or alternate actions, including those discussed elsewhere herein.

For instance, the amount of vehicle usage may include an amount of time and/or miles that each individual vehicle driver drives the vehicle. The type of vehicle usage may include characterizing various periods of driving and/or trips as city driving; country driving; freeway or highway driving city street driving; heavy traffic or congested traffic driving; driving in good weather; driving in hazardous weather; rush hour driving; and/or time-of-day driving.

The vehicle drivers may be identified from mobile device signature; seat pressure sensors and weight; image recognition techniques performed upon images of the driver; and/or biometric devices (such as heart beat or rate characteristics; voice print; and/or thumb or finger prints).

Biometric Device Data

In one aspect, a computer-implemented method of updating an insurance policy using biometric device data may be provided. The method may include (a) gathering or receiving, at or via one or more processors (such as either a local processor associated with a smart vehicle and/or a remote processor or server associated with an insurance provider), data from a biometric device indicative of whom is driving an insured vehicle; (h) gathering or receiving, at or via the one or more processors, data indicative of vehicle usage for a single trip and/or driving or driver behavior during the single trip; (c) updating or adjusting, at or via the one or more processors, an insurance policy (such as a premium, rate, rewards or points program, discount, etc.) for the insured vehicle based upon (1) whom is driving the insured vehicle (and/or his or her driving profile or score), and/or (2) the data indicative of vehicle usage for the single trip and/or the driving or driver behavior exhibited during the single trip to facilitate more accurate risk assessment and/or cost savings to the insured. The method may include additional, fewer, or alternate actions, including those discussed elsewhere herein. For instance, the biometric device may verify an identity of the driver based upon heartbeat, facial recognition techniques, and/or mood.

In another aspect, a computer-implemented method of updating an insurance policy may be provided. The method may include (1) gathering or receiving, at or via one or more processors (such as either a local processor associated with a smart vehicle and/or a remote processor or server associated with an insurance provider), data from a biometric device identifying a driver of an insured vehicle; (2) gathering or receiving, at or via the one or more-processors, data indicative of driving or driver behavior for the driver identified from the biometric device data; (3) generating, at or via the one or more processors, a usage-based insurance policy for the insured vehicle based upon (i) the identity of the driver determined from the biometric device data, and/or (ii) the data indicative of driving or driver behavior exhibited by the driver to facilitate more accurate risk assessment and/or provide cost savings to the insured. The method may include additional, fewer, or alternate actions, including those discussed elsewhere herein.

Usage-Based Insurance for Multiple Drivers

In one aspect, a computer-implemented method of generating or updating an usage-based insurance policy for an autonomous or semi-autonomous vehicle having multiple drivers may be provided. The method may include (1) identifying, via one or more processors (such as a vehicle-mounted local processor or remote insurance provider processor or server), multiple drivers that drive a vehicle, the vehicle having one or more autonomous or semi-autonomous technologies or functionalities; (2) determining, via the one or more processors, a driving behavior for each of the multiple drivers; (3) determining, via the one or more processors, (i) an amount that each autonomous or semi-autonomous technology or functionality is used, and/or (ii) a type of autonomous or semi-autonomous technology or functionality that is employed by each of the multiple drivers; (4) generating or updating, via the one or more processors, an insurance policy (such as a premium, rate, discount, rewards or points program, etc.) for the vehicle based upon (a) the driving behavior for each of the multiple drivers determined, (b) the amount that each autonomous or semi-autonomous technology or functionality is used by each of the multiple drivers, and/or (c) the type of autonomous or semi-autonomous technology or functionality that is employed by each of the multiple drivers to facilitate providing insurance related cost savings to the insured and/or to provide an enticement to an insured family to implement safety enhancing technology or functionality. The method may include additional, fewer, or alternate actions, including those discussed elsewhere herein.

Software Versions

In one aspect, a computer-implemented method of updating an insurance policy may be provided. The method may include (1) gathering or receiving, at or via one or more processors (such as either a local processor associated with a smart vehicle and/or a remote processor or server associated with an insurance provider), data indicative of a software version installed on or in an insured vehicle that is associated with an autonomous or semi-autonomous functionality; (2) determining, at or via the one or more processors, that the software version is out of date or a (safer or less risky) new software version exists and/or is available for download; (3) generating, at or via the one or more processors, a recommendation to an insured to update or upgrade to the new software version, and transmitting that recommendation under the direction or control of the one or more processors to a mobile device or insured vehicle controller (such as via wireless communication or data transmission); (4) determining, at or via the one or more processors, (or receiving an indication) that the insured has updated or upgraded to the new software version associated with the autonomous or semi-autonomous functionality; and/or (5) updating or adjusting, at or via the one or more processors, an insurance policy (such as a premium, rate, rewards or points program, discount, etc.) for the insured vehicle based upon the insured updating or upgrading to the new software version associated with an autonomous or semi-autonomous functionality to facilitate providing cost savings to the insured and/or enticing drivers to update vehicle software to most recent versions and/or versions that perform better. The method may include additional, fewer, or alternate actions, including those discussed elsewhere herein.

Personal Insurance Policies

In one aspect, a computer-implemented method of generating or adjusting a personal insurance policy may be provided. The method may include (1) collecting, gathering, generating, and/or receiving data, via one or more processors (such as a local smart home or smart vehicle controller, and/or a remote insurance provider processor or server), related to home maintenance or upgrades for an insured home of an insured; (2) collecting, gathering, generating, and/or receiving data, via the one or more processors, related to past vehicle maintenance for a vehicle previously or currently owned by the insured; (3) collecting, gathering, generating, and/or receiving data, via the one or more processors, related to driving behavior of the insured; (4) collecting, gathering, generating, and/or receiving data, via the one or more processors, related to autonomous or semi-autonomous vehicle functionality or technology usage by the insured; and/or (5) generating, updating, and/or adjusting, via the one or more processors, an insurance policy (such as a premium, rate, discount, rewards or points program, etc.) based upon (a) the home maintenance or upgrades for the insured home performed by the insured; (b) past vehicle maintenance for the vehicle previously or currently owned by the insured; (c) the driving behavior of the insured; and/or (d) autonomous or semiautonomous vehicle functionality or technology usage by the insured to facilitate providing insurance-related cost savings to the insured. The method may include additional, fewer, or alternate actions, including those discussed elsewhere herein.

In another aspect, a computer-implemented method of generating or adjusting a personal insurance policy may be provided. The method may include (1) collecting, gathering, generating, and/or receiving data, via one or more processors (such as a local smart home or smart vehicle controller, and/or a remote insurance provider processor or server), related to home maintenance or upgrades for an insured home of an insured; (2) collecting, gathering, generating, and/or receiving data, via the one or more processors, related to past vehicle maintenance for one or more vehicles previously or currently owned by the insured; (3) collecting, gathering, generating, and/or receiving data, via the one or more processors, related to driving behavior of the insured;

US 12,663,982 B2

37

(4) collecting, gathering, generating, and/or receiving data, via the one or more processors, related to autonomous or semi-autonomous vehicle functionality or technology usage by the insured; (5) collecting, gathering, generating, and/or receiving data, via the one or more processors, related to one or more lifestyle characteristics and/or risky, or risk averse adverse, behaviors of the insured; and/or (6) generating, updating, and/or adjusting, via the one or more processors, an insurance policy (such as a premium, rate, discount, rewards or points program, etc.) based upon (a) the home maintenance or upgrades for the insured home performed by the insured; (b) past vehicle maintenance for the vehicle previously or currently owned by the insured; (c) the driving behavior of the insured; (d) autonomous or semiautonomous vehicle functionality or technology usage by the insured; and/or (e) one or more lifestyle characteristics and/or risky, or risk averse, behaviors of the insured to facilitate providing insurance-related cost savings to the insured and/or to customers that are generally risk averse. The method may include additional, fewer, or alternate actions, including those discussed elsewhere herein.

The insurance policy generated, updated or adjusted, via the one or more processors, may be a life, auto, home, renters, health, or other type of insurance policy; a personal or holistic insurance policy; and/or a personal insurance policy.

Life Insurance

In one aspect, a computer-implemented method of generating or adjusting a life insurance policy may be provided. The method may include (1) collecting, gathering, generating, and/or receiving data, via one or more processors (such as a local smart home or smart vehicle controller, or mobile device, and/or a remote insurance provider processor or server), related to driving behavior of the insured; (2) collecting, gathering, generating, and/or receiving data, via the one or more processors, related to autonomous or semi-autonomous vehicle functionality or technology usage by the insured; (3) collecting, gathering, generating, and/or receiving data, via the one or more processors, related to one or more lifestyle characteristics and/or risky, or risk averse adverse, behaviors of the insured; and/or (4) generating, updating, and/or adjusting, via the one or more processors, a life insurance policy (such as a premium, rate, discount, rewards or points program, etc.) based upon (i) the driving behavior of the insured; (ii) autonomous or semi-autonomous vehicle functionality or technology usage by the insured; and/or (iii) one or more lifestyle characteristics and/or risky, or risk averse, behaviors of the insured to facilitate providing insurance-related cost savings to the insured and/or to customers that are generally risk averse, and/or to reflect longer life expectancy due to driver usage of autonomous or semi-autonomous vehicle functionality or technology proven to impact driver safety. The method may include additional, fewer, or alternate actions, including those discussed elsewhere herein.

Subscription Insurance Plans for Autonomous Vehicles

In one aspect, a computer-implemented method of providing insurance as a subscription service may be provided. The method may include (1) generating, via one or more processors (such as a local smart home or smart vehicle controller, and/or a remote insurance provider processor or server), one or more insurance subscription plans and/or periodic insurance rates based upon frequency of autonomous vehicle usage and/or frequency of renting autonomous vehicles (such as with persons living in large cities or communities that would rather use an autonomous vehicle taxi service); (2) causing the one or more subscription plans and/or periodic insurance rates, via the one or more processors, to presented on a computing device of an insurance customer or potential customer (and/or otherwise transmitting, such as via wired or wireless communication, the one or more subscription plans and/or periodic insurance rates to the computing device) for review and selection by the insurance customer or potential customer; (3) receiving, via the one or more processors, a selection or approval of a subscription plan and/or periodic insurance rate from the computing device of the insurance customer or potential customer; and/or (4) in response, issuing, via the one or more processors, a subscription insurance plan to the insurance customer or potential customer covering, and/or providing insurance coverage(s) for, the usage and/or rental of the autonomous vehicle(s). For instance, the one or more processors may transmit a copy of the subscription insurance plan to the computing device of the customer for their review and/or records. The method may include additional, fewer, or alternate actions, including those discussed elsewhere herein The subscription insurance plan may include, and/or may have a rate based upon, an amount of autonomous vehicle usage, such as by amount of miles or time (such as by minutes, hours, or days). The subscription insurance plan may provide, include, and/or may be associated with, automatic routing or directions telling or directing the autonomous vehicle to a pickup point and/or a destination for each trip.

The subscription insurance plan charges may be based upon (i) a route taken or directed by the insured or customer; (ii) a time of day that the autonomous vehicle service is provided (e.g., peak hours versus off-peak hours); (iii) an amount of time that the trip takes; and/or (iv) a mileage that autonomous vehicle drives to complete delivering the insured or customer to the destination.

The subscription insurance plan charges may be based upon features and/or capabilities of the autonomous rental vehicles, such as insured or customer selected autonomous and/or rental vehicles, and/or the software versions installed in those vehicles. The subscription insurance plan may include, and/or may be associated with, functionality that verifies the identity of the insured as the insured enters the autonomous vehicle and/or at the pick-up point to prevent fraudulent charges (such as via a biometric device, communication with a mobile device of the insured or customer, facial or voice recognition software, etc.).

Exemplary Autonomous Vehicle Insurance Risk and Price Determination Methods

Risk profiles or risk levels associated with one or more autonomous operation features determined above may be further used to determine risk categories or premiums for vehicle insurance policies covering autonomous vehicles. In some embodiments or under some conditions, the vehicle 108 may be a fully autonomous vehicle operating without a vehicle operator's input or presence. In other embodiments or under other conditions, the vehicle operator may control the vehicle 108 with or without the assistance of the vehicle's autonomous operation features. For example, the vehicle may be fully autonomous only above a minimum speed threshold or may require the vehicle operator to control the vehicle during periods of heavy precipitation. Alternatively, the autonomous vehicle may perform all relevant control functions using the autonomous operation features under all ordinary operating conditions. In still further embodiments, the vehicle 108 may operate in either a fully or a partially autonomous state, while receiving or transmitting autonomous communications.

Where the vehicle 108 operates only under fully autonomous control by the autonomous operation features under ordinary operating conditions or where control by a vehicle operator may be disregarded for insurance risk and price determination, the risk level or premium associated with an insurance policy covering the autonomous vehicle may be determined based upon the risks associated with the autonomous operation features, without reference to risks associated with the vehicle operator. Where the vehicle 108 may be operated manually under some conditions, the risk level or premium associated with an insurance policy covering the autonomous vehicle may be based upon risks associated with both the autonomous operation features and the vehicle operator performing manual vehicle operation. Where the vehicle 108 may be operated with the assistance of autonomous communications features, the risk level or premium associated with an insurance policy covering the autonomous vehicle may be determined based in part upon a determination of the expected use of autonomous communication features by external sources in the relevant environment of the vehicle 108 during operation of the vehicle 108.

Data Acquisition

In one aspect, the present embodiments may relate to data acquisition. Data may be gathered via devices employing wireless communication technology, such as Bluetooth or other IEEE communication standards. In one embodiment, a Bluetooth enabled smartphone or mobile device, and/or an in-dash smart and/or communications device may collect data. The data associated with the vehicle, and/or vehicle or driver performance, that is gathered or collected at, or on, the vehicle may be wirelessly transmitted to a remote processor or server, such as a remote processor or server associated with an insurance provider. The mobile device 110 may receive the data from the on-board computer 114 or the sensors 120, and may transmit the received data to the server 140 via the network 130, and the data may be stored in the database 146. In some embodiments, the transmitted data may include real-time sensor data, a summary of the sensor data, processed sensor data, operating data, environmental data, communication data, or a log such data.

Data may be generated by autonomous or semi-autonomous vehicles and/or vehicle mounted sensors (or smart sensors), and then collected by vehicle mounted equipment or processors, including Bluetooth devices, and/or an insurance provider remote processor or server. The data gathered may be used to analyze vehicle decision making. A processor may be configured to generate data on what an autonomous or semi-autonomous vehicle would have done in a given situation had the driver not taken over manual control/ driving of the vehicle or alternative control actions not taken by the autonomous or semi-autonomous operation features. This type of control decision data (related to vehicle decision making) may be useful with respect to analyzing hypothetical situations.

In one embodiment, an application, or other computer or processor instructions, may interact with a vehicle to receive and/or retrieve data from autonomous or semi-autonomous processors and sensors. The data retrieved may be related to radar, cameras, sensor output, computer instructions or application output. Other data related to a smart vehicle controller, car navigation unit information (including route history information and typical routes taken), GPS unit information, odometer and/or speedometer information, and smart equipment data may also be gathered or collected. The application and/or other computer instructions may be associated with an insurance provider remote processor or server.

The control decision data may further include information regarding control decisions generated by one or more autonomous operation features within the vehicle. The operating data and control decision data gathered, collected, and/or acquired may facilitate remote evaluation and/or analysis of what the autonomous or semi-autonomous vehicle was "trying to do" (brake, slow, turn, accelerate, etc.) during operation, as well as what the vehicle actually did do. The data may reveal decisions, and the appropriateness thereof, made by the artificial intelligence or computer instructions associated with one or more autonomous or semi-autonomous vehicle technologies, functionalities, systems, and/or pieces of equipment. The data may include information related to what the vehicle would have done in a situation if the driver had not taken over (beginning manual vehicle control). Such data may include both the control actions taken by the vehicle and control actions the autonomous or semi-autonomous operation features would have caused the vehicle to take. Thus, in some embodiments, the control decisions data may include information regarding control decisions not implemented by the autonomous operation features to control the vehicle. This may occur when an autonomous operation feature generates a control decision or associated control signal, but the control decision or signal is prevented from controlling the vehicle because the autonomous feature or function is disabled, the control decision is overridden by the vehicle operator, the control signal would conflict with another control signal generated by another autonomous operation feature, a more preferred control decision is generated, and/or an error occurs in the on-board computer 114 or the control system of the vehicle.

For example, a vehicle operator may disable or constrain the operation of some or all autonomous operation features, such as where the vehicle is operated manually or semi-autonomously. The disabled or constrained autonomous operation features may, however, continue to receive sensor data and generate control decision data that is not implemented. Similarly, one or more autonomous operation features may generate more than one control decision in a relevant period of time as alternative control decisions. Some of these alternative control decisions may not be selected by the autonomous operation feature or an autonomous operation control system to control the vehicle. For example, such alternative control decisions may be generated based upon different sets of sensor or communication data from different sensors 120 or include or excluding autonomous communication data. As another example, the alternative control decisions may be generated faster than they can be implemented by the control system of the vehicle, thus preventing all control decisions from being implemented.

In addition to control decision data, other information regarding the vehicle, the vehicle environment, or vehicle operation may be collected, generated, transmitted, received, requested, stored, and/or recorded in connection with the control decision data. Additional operating data including sensor data from the sensors 120, autonomous communication data from the communication component 122 or the communication unit 220, location data, environmental data, time data, settings data, configuration data, and/or other relevant data may be associated with the control decision data. In some embodiments, a database or log may store the control decision data and associated information. In further embodiments, the entries in such log or database may include a timestamp indicating the date, time, location, vehicle environment, vehicle condition, autonomous operation feature settings, and/or autonomous operation feature configuration information associated with each entry. Such data may facilitate evaluating the autonomous or semi-autonomous technology, functionality, system, and/or equipment in hypothetical situations and/or may be used to calculate risk, and in turn adjust insurance policies, premiums, discounts, etc.

Autonomous Vehicle Insurance Policies

The disclosure herein relates to insurance policies for vehicles with autonomous operation features. Accordingly, as used herein, the term "vehicle" may refer to any of a number of motorized transportation devices. A vehicle may be a car, truck, bus, train, boat, plane, motorcycle, snowmobile, other personal transport devices, etc. Also as used herein, an "autonomous operation feature" of a vehicle means a hardware or software component or system operating within the vehicle to control an aspect of vehicle operation without direct input from a vehicle operator once the autonomous operation feature is enabled or engaged. The term "autonomous vehicle" means a vehicle including at least one autonomous operation feature. A "fully autonomous vehicle" means a vehicle with one or more autonomous operation features capable of operating the vehicle in the absence of or without operating input from a vehicle operator.

Additionally, the term "insurance policy" or "vehicle insurance policy," as used herein, generally refers to a contract between an insurer and an insured. In exchange for payments from the insured, the insurer pays for damages to the insured which are caused by covered perils, acts, or events as specified by the language of the insurance policy. The payments from the insured are generally referred to as "premiums," and typically are paid by or on behalf of the insured upon purchase of the insurance policy or over time at periodic intervals. Although insurance policy premiums are typically associated with an insurance policy covering a specified period of time, they may likewise be associated with other measures of a duration of an insurance policy, such as a specified distance traveled or a specified number of trips. The amount of the damages payment is generally referred to as a "coverage amount" or a "face amount" of the insurance policy. An insurance policy may remain (or have a status or state of) "in-force" while premium payments are made during the term or length of coverage of the policy as indicated in the policy. An insurance policy may "lapse" (or have a status or state of "lapsed"), for example, when the parameters of the insurance policy have expired, when premium payments are not being paid, when a cash value of a policy falls below an amount specified in the policy, or if the insured or the insurer cancels the policy.

The terms "insurer," "insuring party," and "insurance provider" are used interchangeably herein to generally refer to a party or entity (e.g., a business or other organizational entity) that provides insurance products, e.g., by offering and issuing insurance policies. Typically, but not necessarily, an insurance provider may be an insurance company. The terms "insured," "insured party," "policyholder," and "customer" are used interchangeably herein to refer to a person, party, or entity (e.g., a business or other organizational entity) that is covered by the insurance policy, e.g., whose insured article or entity is covered by the policy. Typically, a person or customer (or an agent of the person or customer) of an insurance provider fills out an application for an insurance policy. In some cases, the data for an application may be automatically determined or already associated with a potential customer. The application may undergo underwriting to assess the eligibility of the party and/or desired insured article or entity to be covered by the insurance policy, and, in some cases, to determine any specific terms or conditions that are to be associated with the insurance policy, e.g., amount of the premium, riders or exclusions, waivers, and the like. Upon approval by underwriting, acceptance of the applicant to the terms or conditions, and payment of the initial premium, the insurance policy may be in-force, (i.e., the policyholder is enrolled).

Although the exemplary embodiments discussed herein relate to automobile insurance policies, it should be appreciated that an insurance provider may offer or provide one or more different types of insurance policies. Other types of insurance policies may include, for example, commercial automobile insurance, inland marine and mobile property insurance, ocean marine insurance, boat insurance, motorcycle insurance, farm vehicle insurance, aircraft or aviation insurance, and other types of insurance products.

OTHER MATTERS

Although the text herein sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

In one aspect, autonomous or semi-autonomous vehicle; telematics; interconnected home; mobile device; and/or other data, including that discussed elsewhere herein, may be collected or received by an insurance provider remote server, such as via direct or indirect wireless communication or data transmission, after a customer affirmatively consents or otherwise opts into an insurance discount, reward, or other program. The insurance provider may then analyze the data received with the customer's permission to provide benefits to the customer. As a result, risk averse customers may receive insurance discounts or other insurance cost savings based upon data that reflects low risk behavior and/or technology that mitigates or prevents risk to (i) insured assets, such as autonomous or semi-autonomous vehicles, and/or (ii) autonomous or semi-autonomous vehicle operators or passengers.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based upon any statement made in any section of this patent (other than the language of the claims). To the extent that any term recited in the claims at the end of this disclosure is referred to in this disclosure in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based upon the application of 35 U.S.C. § 112(f).

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (code embodied on a non-transitory, tangible machine-readable medium) or hardware. In hardware, the routines, etc., arc tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware" should be understood to encompass a tangible entity, be that an entity that is physically constructed, permanently configured (e.g., hard-wired), or temporarily configured (e.g., programmed) to operate in a certain manner or to perform certain operations described herein. Considering embodiments in which hardware is temporarily configured (e.g., programmed), the hardware need not be configured or instantiated at any one instance in time. Software may accordingly configure a processor, for example, to constitute a particular hardware module at one instance of time and to constitute a different hardware module at a different instance of time. Hardware elements can provide information to, and receive information from, other hardware elements. Accordingly, the described hardware may be regarded as being communicatively coupled.

The various operations of example methods described herein may be performed, at least partially, by one or more processors that are temporarily configured (e.g., by software) or permanently configured to pe1fonn the relevant operations. Whether temporarily or permanently configured, such processors may constitute processor-implemented modules that operate to perform one or more operations or functions. The modules referred to herein may, in some example embodiments, comprise processor-implemented modules. Similarly, the methods or routines described herein may be at least partially processor-implemented. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information. As used herein any reference to "one embodiment" or "an embodiment" means that a particular element, feature, structure, or characteristic described in connection with the embodiment may be included in at least one embodiment. The appearances of the phrase "in one embodiment" in various places in the specification are not necessarily all referring to the same embodiment. Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. In addition, use of the "a" or "an" are employed to describe elements and components of the embodiments herein. This is done merely for convenience and to give a general sense of the description. In this description, and the claims that follow, the singular also includes the plural unless it is obvious that it is meant otherwise. This detailed description is to be construed as exemplary only and does not describe every possible embodiment, as describing every possible embodiment would be impractical, if not impossible. One could implement numerous alternate embodiments, using either current technology or technology developed after the filing date of this application.

Upon reading this disclosure, those of skill in the art will appreciate still additional alternative structural and functional designs for system and a method for assigning mobile device data to a vehicle through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The particular features, structures, or characteristics of any specific embodiment may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention.

What is claimed is:

1. A computer-implemented method for directing a route of an autonomous or semi-autonomous vehicle during an emergency, the method comprising:

receiving, by a processor, an indication that an occupant of the vehicle is experiencing a medical emergency;

identifying, by the processor, a medical facility based on a current location of the vehicle;

determining, by the processor, an estimated time of arrival at the medical facility associated with traversing a route from the current location to the medical facility;

causing, by the processor, the vehicle to traverse the route under autonomous or semi-autonomous control; and transmitting, by the processor and to a remote server, information indicating the traversal of the route under the autonomous or semi-autonomous control, wherein the server modifies an electronic record associated with the occupant based on the information.

2. The computer-implemented method of claim 1, wherein the medical emergency is detected by a sensor of a biometric device carried by the vehicle.

3. The computer-implemented method of claim 1, further comprising:

receiving, by the processor, information indicating that the occupant has agreed to use of an emergency response functionality of the vehicle, wherein the vehicle is caused to traverse the route based on receiving the information.

4. The computer-implemented method of claim 1, further comprising:

transmitting, by the processor, a message to the medical facility indicating the estimated time of arrival.

5. The computer-implemented method of claim 4, wherein the message further includes at least one of: the route, the current location, or information related to the medical emergency.

6. The computer-implemented method of claim 4, wherein the message is further transmitted to a police department, a fire department or a family member of the occupant.

7. The computer-implemented method of claim 1, wherein the current location is determined using at least one of:

a global positioning system (GPS) carried by the vehicle, a GPS unit of a mobile device carried by the vehicle, or a wearable device associated with an occupant of the vehicle.

8. The computer-implemented method of claim 1, wherein the medical emergency includes at least one of: a heart attack, a seizure, or a stroke.

9. The computer-implemented method of claim 1, wherein causing the vehicle to traverse the route comprises:

causing, by the processor, an autonomous operation feature of the vehicle to engage;

causing, by the processor, the autonomous operation feature to control operation of the vehicle along the route; and causing, by the processor, the vehicle to park at a parking location upon arrival at the medical facility.

10. The computer-implemented method of claim 9, wherein the autonomous operation feature performs a function of the vehicle comprising one of:

steering, accelerating, braking, parking, pedestrian detection, vehicle navigation, or vehicle positioning.

11. The computer-implemented method of claim 1, further comprising:

transmitting, by the processor, information related to the medical emergency to the remote server, wherein the medical facility is determined based on communication with the remote server.

12. The computer-implemented method of claim 1, further comprising:

determining, by the processor, a plurality of potential routes from the current location to the medical facility, wherein the plurality of potential routes includes the route.

13. A system for directing a route of an autonomous or semi-autonomous vehicle during an emergency, comprising:

a processor; and computer-readable media storing instructions which, when executed by the processor, causes the processor to:

receive an indication that an occupant of the vehicle is experiencing a medical emergency;

identify a medical facility based at least on a current location of the vehicle;

determine an estimated time of arrival at the medical facility associated with traversing a route from the current location to the medical facility;

cause the vehicle to traverse the route under autonomous or semi-autonomous control; and transmit, to a remote server, information indicating the traversal of the route under the autonomous or semi-autonomous control, wherein the server modifies an electronic record associated with the occupant based on the information.

14. The system of claim 13, wherein the instructions, when executed, further cause the processor to:

transmit a message to the medical facility indicating the estimated time of arrival; and transmit an additional message to at least one of:

a police department, a fire department or a family member of the occupant.

15. The system of claim 14, wherein the message is a first message, the instructions, when executed, further cause the processor to:

transmit a second message to an emergency service requesting assistance at the current location, wherein the second message includes the route and the current location.

16. The system of claim 13, wherein the medical emergency includes at least one of: a heart attack, a seizure, or a stroke.

17. The system of claim 13, wherein the remote server is associated with an insurance provider, and the electronic record corresponds to an insurance policy issued by the insurance provider and associated with the occupant.

18. A non-transitory computer-readable medium storing instructions for directing a route of an autonomous or semi-autonomous vehicle during an emergency which, when executed by a processor, causes the processor to:

receive an indication that an occupant of the vehicle is experiencing a medical emergency;

identify a medical facility based at least on a current location of the vehicle;

determine an estimated time of arrival at the medical facility associated with traversing a route from the current location to the medical facility;

cause the vehicle to traverse the route under autonomous or semi-autonomous control; and transmit to a remote server, information indicating the traversal of the route under the autonomous or semi-autonomous control, wherein the server modifies an electronic record associated with the occupant based on the information.

19. The non-transitory computer-readable medium of claim 18, wherein the medical emergency is detected by a sensor of a biometric device carried by the vehicle.

20. The non-transitory computer-readable medium of claim 18, wherein the instructions, when executed by a processor, further causes the processor to:

transmit, to the medical facility, a message indicating at least one of:

the estimated time of arrival, the route, the current location, or information related to the medical emergency.

* * * * *